United States Patent [19]
Pei et al.

[11] Patent Number: 5,840,500
[45] Date of Patent: Nov. 24, 1998

[54] QUINOLINE DERIVATIVES AND QUINOLINE COMBINATORIAL LIBRARIES

[75] Inventors: Yazhong Pei, Aliso Viejo; John S. Kiely, San Diego, both of Calif.

[73] Assignee: Trega Biosciences, Inc., San Diego, Calif.

[21] Appl. No.: 678,136

[22] Filed: Jul. 11, 1996

[51] Int. Cl.$^6$ .............. G01N 33/53; G01N 33/566; G01N 33/536; G01N 33/531
[52] U.S. Cl. .............. 435/7.1; 436/501; 436/536; 436/543
[58] Field of Search .................. 436/501, 543, 436/536; 435/7.1

[56] References Cited

U.S. PATENT DOCUMENTS

| | | | |
|---|---|---|---|
| 4,692,522 | 9/1987 | Parsons et al. | 540/523 |
| 5,010,175 | 4/1991 | Rutter et al. | 530/334 |
| 5,182,366 | 1/1993 | Huebner et al. | 530/334 |
| 5,231,102 | 7/1993 | Carling et al. | 514/312 |
| 5,288,514 | 2/1994 | Ellman | 427/2 |
| 5,324,483 | 6/1994 | Cody et al. | 422/132 |

FOREIGN PATENT DOCUMENTS

| | | |
|---|---|---|
| 639529 B2 | 5/1991 | Australia. |
| 0 385 630 | 2/1990 | European Pat. Off.. |
| WO 94/01102 | 1/1994 | WIPO. |
| WO 95/02566 | 1/1995 | WIPO. |
| WO 95/04277 | 2/1995 | WIPO. |

OTHER PUBLICATIONS

Leznoff CC, (1974) Use of insoluble polymer supports in organic chemical synthesis. Chem.Soc.Rev. 3: 65–85, 1974.

Gordon et al., "Applications of combinatorial technologies to drug discovery. 2. Combinatorial organic synthesis, library screening strategies, and future directions." *J. of Med. Chem.*, 37(10):1386–1401 (1994).

Gallop et al., "Applications of combinatorial technologies to drug discovery. 1. Background and peptide combinatorial libraries." *J. of Med. Chem.*, 37(9):1233–1251 (1994).

Houghten et al., "Generation and use of synthetic peptide combinatorial libraries for basic research and drug discovery." *Nature*, 354:94–96 (1991).

(List continued on next page.)

*Primary Examiner*—Lora M. Green
*Assistant Examiner*—Joseph W. Ricigliano
*Attorney, Agent, or Firm*—Campbell & Flores LLP

[57] ABSTRACT

The present invention relates to novel tetrahydro-quinoline compounds of the following formula, libraries containing such compounds, and to the generation of such combinatorial libraries composed of such compounds:

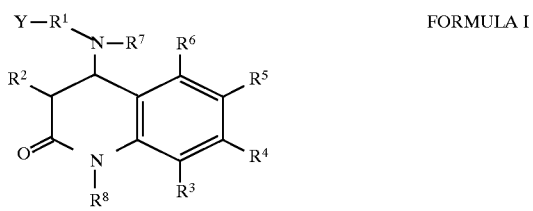

FORMULA I wherein $R^1$, $R^2$, $R^3$, $R^4$, $R^5$, $R^6$, $R^7$, $R^8$ and Y have the meanings provided.

6 Claims, 3 Drawing Sheets

OTHER PUBLICATIONS

Ostresh et al., "Libraries from libraries: Chemical transformation of combinatorial libraries to extend the range and repertoire of chemical diversity." *Proc. Natl. Acad. Sci. USA*, 9:11138–11142 (1994).

Manhas et al., "beta–Lactams as Synthons. Synthesis of Heterocycles via beta–Lactam Cleavage." *Hetercycles*, 5:669–699 (1976).

Clarke et al., "The conversion of 2–(2–chloroacetamido-)benzophenones into 2,3–Dihydro–2–oxo–1,4–benzodiazepines. Part I. With Ammonia." *J. Chem. Research*, 398 (1980).

Kano et al., "Formation of some heterocycles through ring transformation of 1–arylazetidin–2–ones." *Heterocycles*, 8:411–416 (1977).

Ojima and Pei, "Novel rearrangements of chiral 3–oxazolidinylazetidin–2–ones." *Tetrahedron Letters*, 33 (7):887–890 (1992).

Gewald et al., "4–Amino–3–pyridiniochinolin–2(1H)–on–chloride und 3,4–Diaminochinolin–2 (1H)–one." *Chem Res.*, 124:1237–1241 (1991).

Stadlbauer, Wolfgang, "Methoden zur darstellung von 4–Azido–2(1H)–chinolonen [1]," *Monatshefte fur chemie*, 117:1305–1323 (1986).

QUINOLINE DERIVATIVES AND QUINOLINE COMBINATORIAL LIBRARIES

BACKGROUND OF THE INVENTION

1. Field of the Invention

The present invention relates generally to the synthesis of heterocyclic compounds based on the tetrahydro-quinoline ring. More specifically, the invention provides novel tetrahydro-quinolines as well as novel libraries comprised of such compounds.

2. Background Information

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as tetrahydro-quinolines.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such libraries and the rapid screening of the library which identifies lead pharmaceutical peptides.

Combinatorial approaches have recently been extended to "organic," or non-peptide, libraries. The organic libraries to the present, however, are of limited diversity and generally relate to peptidomimetic compounds; in other words, organic molecules that retain peptide chain pharmacophore groups similar to those present in the corresponding peptide.

Combinatorial chemical methods have been applied to a limited number of heterocyclic compounds, as described, for example, in U.S. Pat. No. 5,288,514 to Ellman, U.S. Pat. No. 5,324,483 to Cody et al. and Goff and Zuckermann, *J. Org. Chem.*, 60:5748–5749 (1995). However, the heterocyclic libraries to date contain compounds of limited diversity and complexity.

Substituent limitations have been overcome for mixtures of peptides and peptidomimetics through the use of solid phase techniques versus solution-phase. An important step in the development of solid-phase techniques was the discovery of methods to identify active individual compounds from soluble mixtures of large numbers of compounds, as described, for example, by Rutter in U.S. Pat. No. 5,010,175 and Simon in WO PCT 91/19735. These soluble mixture methods, however, have rarely been applied to the syntheses of complex heterocyclic structures. There exists a need to develop more complex "organic" libraries based on heterocyclic medicinal compounds which would require less time and effort in the synthesis and testing needed to bring an organic pharmaceutical product to fruition. In short, improved methods for generating therapeutically useful heterocyclic compounds, such as tetrahydro-quinoline derivatives, are desired.

This invention satisfies these needs and provides related advantages as well. The present invention overcomes the known limitations to classical organic synthesis of tetrahydro-quinolines and as well as the shortcomings of combinatorial chemistry with heterocycles. The present invention combines the techniques of solid-phase synthesis of heterocycles and the general techniques of synthesis of combinatorial libraries to prepare new tetrahydro-quinoline compounds.

SUMMARY OF THE INVENTION

The present invention relates to novel tetrahydro-quinoline compounds of the following formula, libraries containing at least two or more such compounds, and to the generation of such combinatorial libraries composed of such compounds:

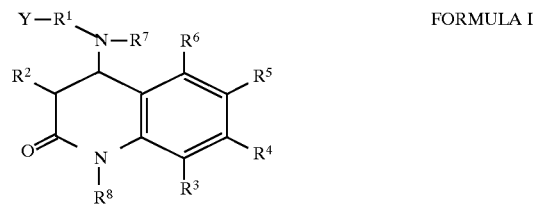

FORMULA I wherein $R^1$, $R^2$, $R^3$, $R^4$, $R^5$, $R^6$, $R^7$, $R^8$ and Y have the meanings provided below.

DETAILED DESCRIPTION OF THE INVENTION

Figure 1:
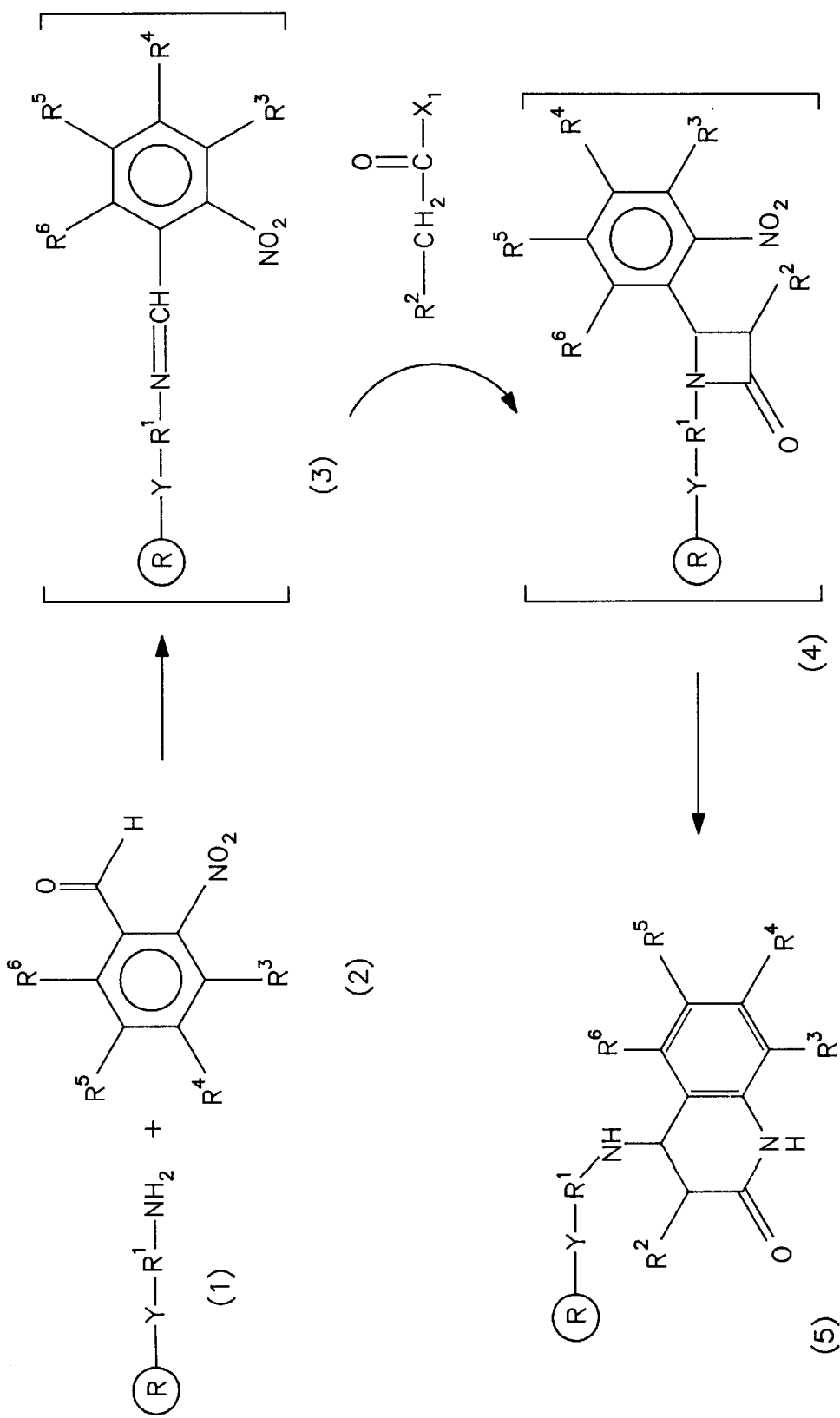
FIG. 1 provides Reaction Scheme I for preparing the tetrahydro-quinoline compounds of the present invention.

The present invention provides novel derivatives and libraries of novel derivatives of variously substituted tetrahydro-quinoline compounds of Formula I:

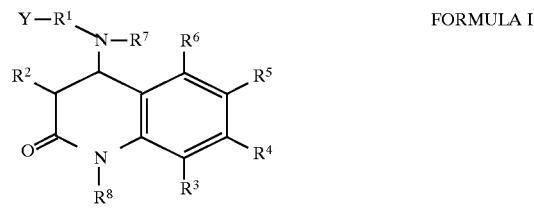

FORMULA I

In the above Formula I:

$R^1$ is $C_1$ to $C_6$ alkyl, $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl or a group of the formula:

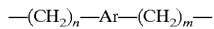

wherein n and m are independently selected from a number 0 to 6; and Ar is an aryl group selected from the group consisting of phenyl, substituted phenyl, heteroaryl or substituted heteroaryl and, more preferably, $R^1$ is $C_1$ to $C_6$ alkyl, $C_1$ to $C_6$ substituted alkyl, $C_3$ to $C_7$ cycloalkyl, $C_3$ to $C_7$ substituted cycloalkyl, phenyl, substituted phenyl, $C_7$ to $C_{12}$ phenylalkyl, $C_7$ to $C_{12}$ substituted phenylalkyl or a group of the formula:

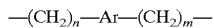

wherein n and m are independently selected from a number 0 to 6; and Ar is an aryl group selected from the group consisting of phenyl, substituted phenyl, heteroaryl or substituted heteroaryl;

$R^2$ is hydroxy, $C_1$ to $C_7$ alkoxy, $C_1$ to $C_7$ substituted alkoxy, C1 to $C_7$ acyloxy, $C_7$ to $C_{12}$ phenylalkoxy, $C_7$ to $C_{12}$ substituted phenylalkoxy, phenoxy, substituted phenoxy, phthalimide, substituted phthalimide, amino, protected amino, (monosubstituted)amino, (disubstituted)amino, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl or substituted phenylsulfonyl;

$R^3$, $R^4$, $R^5$ and $R^6$ are, independently, a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ alkoxy, $C_1$ to $C_7$ substituted alkoxy, C1 to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl or substituted phenylsulfonyl and, more preferably, $R^3$, $R^4$, $R^5$ and $R^6$ are, independently, a hydrogen atom, halo, hydroxy, protected hydroxy, cyano, nitro, $C_1$ to $C_6$ alkyl, $C_1$ to $C_6$ substituted alkyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, a heterocyclic ring, $C_7$ to $C_{12}$ phenylalkyl, $C_7$ to $C_{12}$ substituted phenylalkyl, phenyl, substituted phenyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, or protected carboxamide;

$R^7$ and $R^8$ are, independently, a hydrogen atom, $C_1$ to $C_6$ alkyl, $C_1$ to $C_6$ substituted alkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, substituted phenylaminocarbonyl; and Y is $CO_2H$, OH, SH, $NHR^9$, $C(O)NHR^9$, $CH_2OH$, $CH_2NH_2$, $CH_2NHR^9$ or a functionalized resin, wherein $R^9$ is a hydrogen atom, $C_1$ to $C_6$ alkyl or $C_1$ to $C_6$ substituted alkyl, and more preferably, Y is $CO_2H$, $NHR^9$ or $C(O)NHR^9$, wherein $R^9$ is a hydrogen atom, $C_1$ to $C_6$ alkyl or $C_1$ to $C_6$ substituted alkyl.

For $R^1$ defined above, n and m are independently selected from a number 0 to 6. Preferably, n and m are independently selected from 0 to 4 and, more preferably, from 0 to 3.

In a preferred embodiment of this invention, the tetrahydro-quinoline compounds and libraries containing the same are wherein:

$R^1$ is $C_1$ to $C_6$ alkyl, $C_1$ to $C_6$ substituted alkyl, $C_3$ to $C_7$ cycloalkyl, $C_3$ to $C_7$ substituted cycloalkyl, phenyl, substituted phenyl, $C_7$ to Cl$_2$ phenylalkyl, $C_7$ to $C_{12}$ substituted phenylalkyl or a group of the formula:

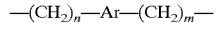

wherein n and m are independently selected from a number 0 to 6; and Ar is an aryl group selected from the group consisting of phenyl, substituted phenyl, heteroaryl or substituted heteroaryl;

$R^2$ is hydroxy, $C_1$ to $C_7$ alkoxy, $C_1$ to $C_7$ acyloxy, $C_7$ to $C_{12}$ phenylalkoxy, $C_7$ to $C_{12}$ substituted phenylalkoxy, phenoxy or substituted phenoxy;

$R^3$, $R^4$, $R^5$ and $R^6$ are, independently, a hydrogen atom, halo, hydroxy, protected hydroxy, or $C_1$ to $C_7$ alkoxy;

$R^7$ and $R^8$ are, independently, a hydrogen atom; and

Y is $C(O)NHR^9$, wherein $R^9$ is a hydrogen atom.

In yet another preferred embodiment of this invention, the tetrahydro-quinoline compounds and libraries containing the same are wherein:

$R^1$ is 1,2-ethyl, 1,3-propyl, 1,4-butyl, 1,5-pentyl, 1,6-hexyl, 1-methyl-1,1-ethyl, 3-aminobenzoyl, 4-amino-2-chlorobenzoyl, 4-aminobenzoyl, 4-aminomethylbenzoyl, D-1,1-butyl, D-1,1-ethyl, D-1,1-pentyl, D-1,1-propyl, D-1-amino-1,5-pentyl, D-2-(2-naphthyl)-1,1-ethyl, D-2-(2-thienyl)-1,1-ethyl, D-2-(3-pyridyl)-1,1-ethyl, D-2-(4-aminophenyl)-1,1-ethyl, D-2-(4-chlorophenyl)-1,1-ethyl, D-2-(4-ethoxyphenyl)-1,1-ethyl, D-2-(4-fluorophenyl)-1,1-ethyl, D-2-(4-hydroxyphenyl)-1,1-ethyl, D-2-(N-formyl-indol-3-yl)-1,1-ethyl, D-2-carboxamido-1,1-ethyl, D-2-carboxamido-1,2-ethyl, D-2-carboxy-1,2-ethyl, D-2-cyclohexyl-1,1-ethyl, D-2-hydroxy-1,1-ethyl, D-2-hydroxy-1,1-propyl, D-2-mercapto-1,1-ethyl, D-2-methyl-1,1-butyl, D-2-methyl-1,1-propyl, D-2-phenyl-1,1-ethyl, D-3-carboxamido-1,1-propyl, D-3-carboxamido-1,3-propyl, D-3-carboxy-1,1-propyl, D-3-carboxy-1,3-propyl, D-3-methyl-1,1-butyl, D-4-ureido-1,1-butyl, D-5-(9- fluorenylmethoxycarboxamido)-1,1-pentyl, D-5-acetamido-1,1-pentyl, D-5-amino-1,1-pentyl, D-methylthio-1,1-propyl, D-phenylmethyl, D-t-butylmethyl, L-1,1-butyl, L-1,1-ethyl, L-1,1-pentyl, L-1,1-propyl, L-1-amino-1,5-pentyl, L-2-(2-naphthyl)-1,1-ethyl, L-2-(2-thienyl)-1,1-ethyl, L-2-(3-pyridyl)-1,1-ethyl, L-2-(4-aminophenyl)-1,1-ethyl, L-2-(4-chlorophenyl)-1,1-ethyl, L-2-(4-ethoxyphenyl)-1,1-ethyl, L-2-(4-fluorophenyl)-1,1-ethyl, L-2-(4-hydroxyphenyl)-1,1-ethyl, L-2-(N-formyl-indol-3-yl)-1,1-ethyl, L-2-carboxamido-1,1-ethyl, L-2-carboxamido-1,2-ethyl, L-2-carboxy-1,1-ethyl, L-2-carboxy-1,2-ethyl, L-2-cyclohexyl-1,1-ethyl, L-2-hydroxy-1,1-ethyl, L-2-hydroxy-1,1-propyl, L-2-mercapto-1,1-ethyl, L-2-methyl-1,1-butyl, L-2-methyl-1,1-propyl, L-2-phenyl-1,1-ethyl, L-3-carboxamido-1,1-propyl, L-3-carboxamido-1,3-propyl, L-3-carboxy-1,1-propyl, L-3-carboxy-1,3-propyl, L-3-methyl-1,1-butyl, L-4-ureido-1,1-butyl, L-5-acetamido-1,1-pentyl, L-5-amino-1,1-pentyl, 5-(4-amino-(3,4-dihydro-3-alkoxy)-2-quinolinoyl)-1,1-pentyl, L-methylthio-1,1-propyl, L-phenylmethyl, L-t-butylmethyl, or methylene;

$R^2$ is hydroxy, methoxy, phenoxy, benzyloxy, acetoxy or 4-chlorophenoxy;

$R^3$ $R^4$, $R^5$, $R^6$ are each, independently, a hydrogen atom, or $R^3$ and $R^6$ are each hydrogen when $R^4$ and $R^5$ are together methylenedioxy or when $R^4$ and $R^5$ are, independently, methoxy, or, alternatively, $R^3$, $R^4$ and $R^6$ are each a hydrogen atom when $R^5$ is chloro or methoxy, and $R^3$ is methoxy when $R^4$, $R^5$ and $R^6$ are each, independently, a hydrogen atom;

$R^7$ is a hydrogen atom;

$R^8$ is a hydrogen atom; and

Y is $C(O)NH_2$.

In a further preferred embodiment, $R^1$ is 1,2-ethyl, 1,3-propyl, 1,4-butyl, 1,5-pentyl, 1,6-hexyl, 1-methyl-1,1-ethyl, 3-aminobenzoyl, 4-amino-2-chlorobenzoyl, 4-aminobenzoyl, 4-aminomethylbenzoyl, D-1,1-butyl, D-1,1-ethyl, D-1,1-pentyl, D-1,1-propyl, D-1-amino-1,5-pentyl, D-2-(2-naphthyl)-1,1-ethyl, D-2-(2-thienyl)-1,1-ethyl, D-2-(3-pyridyl)-1,1-ethyl, D-2-(4-aminophenyl)-1,1-ethyl, D-2-(4-chlorophenyl)-1,1-ethyl, D-2-(4-ethoxyphenyl)-1,1-ethyl, D-2-(4-fluorophenyl)-1,1-ethyl, D-2-(4-hydroxyphenyl)-1,1-ethyl, D-2-(N-formyl-indol-3-yl)-1,1-ethyl, D-2-carboxamido-1,1-ethyl, D-2-carboxamido-1,2-ethyl, D-2-carboxy-1,2-ethyl, D-2-cyclohexyl-1,1-ethyl, D-2-hydroxy-1,1-ethyl, D-2-hydroxy-1,1-propyl, D-2-mercapto-1,1-ethyl, D-2-methyl-1,1-butyl, D-2-methyl-1,1-propyl, D-2-phenyl-1,1-ethyl, D-3-carboxamido-1,1-propyl, D-3-carboxamido-1,3-propyl, D-3-carboxy-1,1-propyl, D-3-carboxy-1,3-propyl, D-3-methyl-1,1-butyl, D-4-ureido-1,1-butyl, D-5-(9-fluorenylmethoxycarboxamido)-1,1-pentyl, D-5-acetamido-1,1-pentyl, D-5-amino-1,1-pentyl, D-methylthio-1,1-propyl, D-phenylmethyl, D-t-butylmethyl, L-1,1-butyl, L-1,1-ethyl, L-1,1-pentyl, L-1,1-propyl, L-1-amino-1,5-pentyl, L-2-(2-naphthyl)-1,1-ethyl, L-2-(2-thienyl)-1,1-ethyl, L-2-(3-pyridyl)-1,1-ethyl, L-2-(4-aminophenyl)-1,1-ethyl, L-2-(4-chlorophenyl)-1,1-ethyl, L-2-(4-ethoxyphenyl)-1,1-ethyl, L-2-(4-fluorophenyl)-1,1-ethyl, L-2-(4-hydroxyphenyl)-1,1-ethyl, L-2-(N-formyl-indol-3-yl)-1,1-ethyl, L-2-carboxamido-1,1-ethyl, L-2-carboxamido-1,2-ethyl, L-2-carboxy-1,1-ethyl, L-2-carboxy-1,2-ethyl, L-2-cyclohexyl-1,1-ethyl, L-2-hydroxy-1,1-ethyl, L-2-hydroxy-1,1-propyl, L-2-mercapto-1,1-ethyl, L-2-methyl-1,1-butyl, L-2-methyl-1,1-propyl, L-2-phenyl-1,1-ethyl, L-3-carboxamido-1,1-propyl, L-3-carboxamido-1,3-propyl, L-3-carboxy-1,1-propyl, L-3-carboxy-1,3-propyl, L-3-methyl-1,1-butyl, L-4-ureido-1,1-butyl, L-5-acetamido-1,1-pentyl, L-5-amino-1,1-pentyl, 5-(4-amino-(3,4-dihydro-3-alkoxy)-2-quinolinoyl)-1,1-pentyl, L-methylthio-1,1-propyl, L-phenylmethyl, L-t-butylmethyl, or methylene;

$R^2$ is hydroxy, methoxy, phenoxy, benzyloxy, acetoxy or 4-chlorophenoxy;

$R^3$ $R^4$, $R^5$, $R^6$ are each, independently, a hydrogen atom, or $R^3$ and $R^6$ are each hydrogen when $R^4$ and $R^5$ are together methylenedioxy or when $R^4$ and $R^5$ are, independently, methoxy, or, alternatively, $R^3$, $R^4$ and $R^6$ are each a hydrogen atom when $R^5$ is chloro or methoxy, or $R^3$ is methoxy when $R^4$, $R^5$ and $R^6$ are each, independently, a hydrogen atom;

$R^7$ is nalidixoyl, 2-phenyl-4-quinolinecarboxy, 2-pyrazinecarboxy, niflumoyl, 4-nitrophenylacetyl, 4-(4-nitrophenyl)butyroyl,(3,4-dimethoxyphenyl)acetyl, 3,4-(methylenedioxy)phenylacetyl, 4-nitrocinnamoyl, 3,4,-(methylenedioxy)cinnamoyl, 3,4,5-trimethoxycinnamoyl, benzoyl, 2-chlorobenzoyl, 2-nitrobenzoyl, 2-(p-toluoyl)benzoyl, 2,4-dinitrophenylacetyl, 3-(3,4,5-trimethoxyphenyl)-propionyl, 4-biphenylacetyl, 1-napthylacetyl, (2-napthoxy)acetyl, trans-cinnamoyl, picolinyl, 3-amino-4-hydroxybenzoyl, (4-pyridylthio)acetyl, 2,4-dichlorobenzoyl, 3,4-dichlorobenzoyl, 4-biphenylcarboxy, thiophenoxyacetyl, 1-benzoylpropionyl, phenylacetyl, hydrocinnamoyl, 3,3-diphenylpropionyl, 3,3,3-triphenylpropionyl, 4-phenylbutyryl, phenoxyacetyl, (±)-2-phenoxypropionyl, 2,4-dimethoxybenzoyl, 3,4-dimethoxybenzoyl, 3,4-dihydroxybenzoyl, 2,4-dihydroxybenzoyl, 3,4,5-trimethoxybenzoyl, 3,4,5-triethoxybenzoyl, 3,4,5-trihydroxybenzoyl, 2-benzoylbenzoyl, 1-napthoyl, xanthene-9-carboxy, 4-chloro-2-nitrobenzoyl, 2-chloro-4-nitrobenzoyl, 4-chloro-3-nitrobenzoyl, 2-chloro-5-nitrobenzoyl, 4-dimethylaminobenzoyl, 4-(diethylamino)benzoyl, 4-nitrobenzoyl, 3-(dimethylamino)benzoyl, p-methylbenzoyl, p-methoxybenzoyl, trimethylacetyl, tert-butylacetyl, (−)-menthoxyacetyl, cyclohexanecarboxy, cyclohexylacetyl, dicyclohexylacetyl, 4-cyclohexylbutyroyl, cycloheptanecarboxy, 13-isopropylpodocarpa-7,13-dien-15-oyl, acetyl, octanoyl, (methylthio)acetyl, 3-nitropropionyl, 4-amino-3 hydroxybenzoyl, 3-(2-methyl-4-nitro-1-imidizoyl)propionyl, 2-furoyl, (s)(−)-2-pyrrolidone-5-carboxy, (2-pyrimidylthio)acetyl, 4-methoxy-2-quinolinecarboxy, 1-adamantanecarboxy, piperonoyl, 5-methyl-3-phenylisoxazole-4-carboxy, rhodanine-3-acetyl, 2-norbornaneacetyl, nicotinoyl, 9-oxo-9H-thioxanthene-3-carboxyl-10,10 dioxide, 2-thiophenecarboxy, 5-nitro-2-furanoyl, indole-3-acetyl, isonicotinoyl, 3a-hydroxy-5β-cholan-24-oyl, (3α,7α,12α)-trihydroxy-5β-cholan-24-oyl, (3α,5β-12α)-3,12, dihydroxy-5-cholan-24-oyl, (3α,5β,6α)-3,6-dihydroxy-cholan-24-oyl, L-alaninyl, L-cysteinyl, L-aspartinyl, L-glutaminyl, L-phenylalaninyl, glycinyl, L-histidinyl, L-isoleucinyl, L-lyscinyl, L-leucinyl, L-methionylsulfoxide, L-methionyl, L-asparginyl, L-prolinyl, L-glutaminyl, L-arganinyl, L-serinyl, L-threoninyl, L-valinyl, L-tryptophanoyl, L-tyrosinyl, D-alaninyl, D-cysteinyl, D-aspartinyl, D-glutaminyl, D-phenylalaninyl, glycinyl, D-histidinyl, D-isoleucinyl, D-lyscinyl, D-leucinyl, D-methionylsulfoxide, D-methionyl, D-asparginyl, D-prolinyl, D-glutaminyl, D-arganinyl, D-serinyl, D-threoninyl, D-valinyl, D-tryptophanoyl, D-tyrosinyl, 2-aminobutyroyl, 4-aminobutyroyl, 2-aminoisobutyroyl, L-norleucinyl, D-norleucinyl, 6-aminohexanoyl, 7-aminoheptanoyl, thioprolinyl, L-norvalinyl, D-norvalinyl, α-ornithinyl, methionyl sulfonyl, L-naphthylalaninyl, D-naphthylalaninyl, L-phenylglycinyl, D-phenylglycinyl, β-alaninyl, L-cyclohexylalaninyl, D-cyclohexylalaninyl, hydroxyprolinyl, 4-nitrophenylalaninyl, dehydroprolinyl, 3-hydroxy-1-propanesulfonyl, 1-propanesulfonyl, 1-octanesulfonyl, perfluoro-1-octanesulfonly, (+)-10-camphorsulfonyl, (−)-10-camphorsulfonyl, benzenesulfonyl, 2-nitrobenzenesulfonyl, p-toluenesulfonyl, 4-nitrobenzenesulfonyl, n-acetylsulfanilyl, 2,5-dichlorobenzenesulfonyl, 2,4-dinitrobenzenesulfonyl, 2-mesitylenesulfonyl or 2-napthalenesulfonyl;

$R^8$ is a hydrogen atom; and

Y is $C(O)NH_2$.

In yet another preferred embodiment, $R^1$ is 1,2-ethyl, 1,3-propyl, 1,4-butyl, 1,5-pentyl, 1,6-hexyl, 1-methyl-1,1-ethyl, 3-aminobenzoyl, 4-amino-2-chlorobenzoyl, 4-aminobenzoyl, 4-aminomethylbenzoyl, D-1,1-butyl, D-1,1-ethyl, D-1,1-pentyl, D-1,1-propyl, D-1-amino-1,5-pentyl, D-2-(2-naphthyl)-1,1-ethyl, D-2-(2-thienyl)-1,1-ethyl, D-2-(3-pyridyl)-1,1-ethyl, D-2-(4-aminophenyl)-1,1-ethyl, D-2-(4-chlorophenyl)-1,1-ethyl, D-2-(4-ethoxyphenyl)-1,1-ethyl, D-2-(4-fluorophenyl)-1,1-ethyl, D-2-(4-hydroxyphenyl)-1,1-ethyl, D-2-(N-formyl-indol-3-yl)-1,1-ethyl, D-2-carboxamido-1,1-ethyl, D-2-carboxamido-1,2-ethyl, D-2-carboxy-1,2-ethyl, D-2-cyclohexyl-1,1-ethyl, D-2-hydroxy-1,1-ethyl, D-2-hydroxy-1,1-propyl, D-2-mercapto-1,1-ethyl, D-2-methyl-1,1-butyl, D-2-methyl-1,1-propyl, D-2-phenyl-1,1-ethyl, D-3-carboxamido-1,1-propyl, D-3-carboxamido-1,3-propyl, D-3-carboxy-1,1-propyl, D-3-carboxy-1,3-propyl, D-3-methyl-1,1-butyl, D-4-ureido-1,1-butyl, D-5-(9-fluorenylmethoxycarboxamido)-1,1-pentyl, D-5-acetamido-1,1-pentyl, D-5-amino-1,1-pentyl, D-methylthio-1,1-propyl, D-phenylmethyl, D-t-butylmethyl, L-1,1-butyl, L-1,1-ethyl, L-1,1-pentyl, L-1,1-propyl, L-1-amino-1,5-pentyl, L-2-(2-naphthyl)-1,1-ethyl, L-2-(2-thienyl)-1,1-ethyl, L-2-(3-pyridyl)-1,1-ethyl, L-2-(4-aminophenyl)-1,1-ethyl, L-2-(4-chlorophenyl)-1,1-ethyl, L-2-(4-ethoxyphenyl)-1,1-ethyl, L-2-(4-fluorophenyl)-1,1-ethyl, L-2-(4-hydroxyphenyl)-1,1-ethyl, L-2-(N-formyl-indol-3-yl)-1,1-ethyl, L-2-carboxamido-1,1-ethyl, L-2-carboxamido-1,2-ethyl, L-2-carboxy-1,1-ethyl, L-2-carboxy-1,2-ethyl, L-2-cyclohexyl-1,1-ethyl, L-2-hydroxy-1,1-ethyl, L-2-hydroxy-1,1-propyl, L-2-mercapto-1,1-ethyl, L-2-methyl-1,1-butyl, L-2-methyl-1,1-propyl, L-2-phenyl-1,1-ethyl, L-3-carboxamido-1,1-propyl, L-3-carboxamido-1,3-propyl, L-3-carboxy-1,1-propyl, L-3-carboxy-1,3-propyl, L-3-methyl-1,1-butyl, L-4-ureido-1,1-butyl, L-5-acetamido-1,1-pentyl, L-5-amino-1,1-pentyl, 5-(4-amino-(3,4-dihydro-3-alkoxy)-2quinolinoyl)-1,1-pentyl, L-methylthio-1,1-propyl, L-phenylmethyl, L-t-butylmethyl, or methylene;

$R^2$ is hydroxy, methoxy, phenoxy, benzyloxy, acetoxy or 4-chlorophenoxy;

$R^3$ $R^4$, $R^5$, $R^6$ are each, independently, a hydrogen atom, or $R^3$ and $R^6$ are each hydrogen when $R^4$ and $R^5$ are together methylenedioxy or when $R^4$ and $R^5$ are, independently, methoxy, or, alternatively, $R^3$, $R^4$ and $R^6$ are each a hydrogen atom when $R^5$ is chloro or methoxy, or $R^3$ is methoxy when $R^4$, $R^5$ and $R^6$ are each, independently, a hydrogen atom;

$R^7$ and $R^8$ are, independently, nalidixoyl, 2-phenyl-4-quinolinecarboxy, 2-pyrazinecarboxy, niflumoyl, 4-nitrophenylacetyl, 4-(4-nitrophenyl)butyroyl,(3,4-dimethoxyphenyl)acety 1, 3,4-(methylenedioxy) phenylacetyl, 4-nitrocinnamoyl, 3,4,-(methylenedioxy) cinnamoyl, 3,4,5-trimethoxycinnamoyl, benzoyl, 2-chlorobenzoyl, 2-nitrobenzoyl, 2-(p-toluoyl)benzoyl, 2,4-dinitrophenylacetyl, 3-(3,4,5-trimethoxyphenyl)-propionyl, 4-biphenylacetyl, 1-napthylacetyl, (2-napthoxy)acetyl, trans-cinnamoyl, picolinyl, 3-amino-4-hydroxybenzoyl, (4-pyridylthio)acetyl, 2,4-dichlorobenzoyl, 3,4-dichlorobenzoyl, 4-biphenylcarboxy, thiophenoxyacetyl, 1-benzoylpropionyl, phenylacetyl, hydrocinnamoyl, 3,3-diphenylpropionyl, 3,3,3-triphenylpropionyl, 4-phenylbutyryl, phenoxyacetyl, (±)-2-phenoxypropionyl, 2,4-dimethoxybenzoyl, 3,4-dimethoxybenzoyl, 3,4-dihydroxybenzoyl, 2,4-dihydroxybenzoyl, 3,4,5-trimethoxybenzoyl, 3,4,5-triethoxybenzoyl, 3,4,5-trihydroxybenzoyl, 2-benzoylbenzoyl, 1-napthoyl, xanthene-9-carboxy, 4-chloro-2-nitrobenzoyl, 2-chloro-4-nitrobenzoyl, 4-chloro-3-nitrobenzoyl, 2-chloro-5-nitrobenzoyl, 4-(dimethylamino)benzoyl, 4-(diethylamino)benzoyl, 4-nitrobenzoyl, 3-dimethylaminobenzoyl, p-methylbenzoyl, p-methoxybenzoyl, trimethylacetyl, tert-butylacetyl, (−)-menthoxyacetyl, cyclohexanecarboxy, cyclohexylacetyl, dicyclohexylacetyl, cyclohexanebutyroyl, cycloheptanecarboxy, 13-isopropylpodocarpa-7,13-dien-15-oyl, acetyl, octanoyl, (methylthio)acetyl, 3-nitropropionyl, 4-amino-3-hydroxybenzoyl, 3-(2-methyl-4-nitro-1-imidizoyl)propionyl, 2-furoyl, (s)(−)-2-pyrrolidone-5-carboxy, (2-pyrimidylthio)acetyl, 4-methoxy-2-quinolinecarboxy, 1-adamantanecarboxy, piperonoyl, 5-methyl-3-phenylisoxazole-4-carboxy, rhodanine-3-acetyl, 2-norbornaneacetyl, nicotinoyl, 9-oxo-9H-thioxanthene-3-carboxyl-10,10 dioxide, 2-thiophenecarboxy, 5-nitro-2-furanoyl, indole-3-acetyl, isonicotinoyl, 3α-hydroxy-5β-cholan-24-oyl, 3α,7α,12α)-trihydroxy-5β-cholan-24-oyl, 3α,5β-12α)-3,12, dihydroxy-5-cholan-24-oyl, 3α,5β,6α)-3,6-dihydroxy-cholan-24-oyl, L-alaninyl, L-cysteinyl, L-aspartinyl, L-glutaminyl, L-phenylalaninyl, glycinyl, L-histidinyl, L-isoleucinyl, L-lyscinyl, L-leucinyl, L-methionylsulfoxide, L-methionyl, L-asparginyl, L-prolinyl, L-glutaminyl, L-arganinyl, L-serinyl, L-threoninyl, L-valinyl, L-tryptophanoyl, L-tyrosinyl, D-alaninyl, D-cysteinyl, D-aspartinyl, D-glutaminyl, D-phenylalaninyl, glycinyl, D-histidinyl, D-isoleucinyl, D-lyscinyl, D-leucinyl, D-methionylsulfoxide, D-methionyl, D-asparginyl, D-prolinyl, D-glutaminyl, D-arganinyl, D-serinyl, D-threoninyl, D-valinyl, D-tryptophanoyl, D-tyrosinyl, 2-aminobutyroyl, 4-aminobutyroyl, 2-aminoisobutyroyl, L-norleucinyl, D-norleucinyl, 6-aminohexanoyl, 7-aminoheptanoyl, thioprolinyl, L-norvalinyl, D-norvalinyl, α-ornithinyl, methionyl sulfonyl, L-naphthylalaninyl, D-naphthylalaninyl, L-phenylglycinyl, D-phenylglycinyl, β-alaninyl, L-cyclohexylalaninyl, D-cyclohexylalaninyl, hydroxyprolinyl, nitrophenylalaninyl, dehydroprolinyl, 3-hydroxy-1-propanesulfonyl, 1-propanesulfonyl, 1-octanesulfonyl, perfluoro-1-octanesulfonly, (+)-10-camphorsulfonyl, (−)-10-camphorsulfonyl, benzenesulfonyl, 2-nitrobenzenesulfonyl, p-toluenesulfonyl, 4-nitrobenzenesulfonyl, n-acetylsulfanilyl, 2,5-dichlorobenzenesulfonyl, 2,4-dinitrobenzenesulfonyl, 2-mesitylenesulfonyl or 2-napthalenesulfonyl; and Y is C(O)NH$_2$.

In the above Formula I, the R$^1$—X substituents are such that X is always bonded to the 1-position of the R$^1$ radical. All naming above and hereinafter reflects this positioning between the two substituents.

In the above Formula I, the stereochemistry of chiral centers associated with the R$^1$ through R$^8$ groups can independently be in the R or S configuration, or a mixture of the two.

In the above Formula I, the term "C$_1$ to C$_6$ alkyl" denotes such radicals as methyl, ethyl, n-propyl, isopropyl, n-butyl, sec-butyl, tert-butyl, amyl, tert-amyl, hexyl and the like. The preferred "C$_1$ to C$_6$ alkyl" group is methyl.

The term "C$_2$ to C$_7$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "C$_2$ to C$_7$ alkynyl" denotes such radicals as ethynyl, propynyl, butynyl, pentynyl, hexynyl, heptynyl, as well as di- and tri-ynes of straight and branched chains.

The term "C$_1$ to C$_6$ substituted alkyl," "C$_2$ to C$_7$ substituted alkenyl," and "C$_2$ to C$_7$ substituted alkynyl," denotes that the above C$_1$ to C$_6$ alkyl groups and C$_2$ to C$_7$ alkenyl and alkynyl groups are substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, C$_1$ to C$_7$ alkoxy, C$_1$ to C$_7$ acyl, C$_1$ to C$_7$ acyloxy, nitro, C$_1$ to C$_7$ alkyl ester, carboxy, protected carboxy, carbamoyl, carboxamide, protected carboxamide, N-(C$_1$ to C$_6$ alkyl)carboxamide, protected N-(C$_1$ to C$_6$ alkyl)carboxamide, N,N-di(C$_1$ to C$_6$ alkyl)carboxamide, cyano, methylsulfonylamino, thio, C$_1$ to C$_4$ alkylthio or C$_1$ to C$_4$ alkyl sulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, formyl, acetyl, benzoyl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, chloroethyl, bromoethyl, fluoroethyl, iodoethyl, chloropropyl, bromopropyl, fluoropropyl, iodopropyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "C$_1$ to C$_7$ alkoxy" as used herein denotes groups such as methoxy, ethoxy, n-propoxy, isopropoxy, n-butoxy, t-butoxy and like groups. A preferred alkoxy is methoxy. The term "C$_1$ to C$_7$ substituted alkoxy" means the alkyl portion of the alkoxy can be substituted in the same manner as in relation to C$_1$ to C$_6$ substituted alkyl.

The term "C$_1$ to C$_7$ acyloxy" denotes herein groups such as formyloxy, acetoxy, propionyloxy, butyryloxy, pentanoyloxy, hexanoyloxy, heptanoyloxy and the like.

Similarly, the term "C$_1$ to C$_7$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "C$_1$ to C$_7$ substituted acyl" denotes the acyl group substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, C$_1$ to C$_7$ alkoxy, C$_1$ to C$_7$ acyl, C$_1$ to C$_7$ acyloxy, nitro, C$_1$ to C$_7$ alkyl ester, carboxy, protected carboxy, carbamoyl, carboxamide, protected carboxamide, N-(C$_1$ to C$_6$ alkyl)carboxamide, protected N-(C$_1$ to C$_6$ alkyl)carboxamide, N,N-di(C$_1$ to C$_6$ alkyl)carboxamide, cyano, methylsulfonylamino, thio, C$_1$ to C$_4$ alkylthio or C$_1$ to C$_4$ alkyl sulfonyl groups. The substituted acyl groups may be substituted once or more, and preferably once or twice, with the same or with different substituents.

Examples of C$_1$ to C$_7$ substituted acyl include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

The substituent term "C$_3$ to C$_7$ cycloalkyl" includes the cyclopropyl, cyclobutyl, cyclopentyl, cyclohexyl or cycloheptyl rings. The substituent term "C$_3$ to C$_7$ substituted cycloalkyl" indicates the above cycloalkyl rings substituted by one or two halogen, hydroxy, protected hydroxy, C$_1$ to C$_6$ alkyl, C$_1$ to C$_7$ alkoxy, oxo, protected oxo, (monosubstituted)amino, (disubstituted)amino, trifluoromethyl, carboxy, protected carboxy, phenyl, substituted phenyl, amino, or protected amino groups.

The term "C$_5$ to C$_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted C$_5$ to C$_7$ cycloalkenyl" denotes the above C$_5$ to C$_7$ cycloalkenyl rings substituted by a C$_1$ to C$_6$ alkyl radical, halogen, hydroxy, protected hydroxy, C$_1$ to C$_7$ alkoxy, trifluoromethyl, carboxy, protected carboxy, oxo, protected oxo, (monosubstituted)amino, protected (monosubstituted) amino, (disubstituted)amino, phenyl, substituted phenyl, amino, or protected amino.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be saturated, fully saturated or partially unsaturated, with fully saturated rings being preferred. An "amino-substituted heterocyclic ring" means any one of the above-described heterocyclic rings is substituted with at least one amino group. Preferred heterocyclic rings include morpholino, piperidinyl, piperazinyl, tetrahydrofurano, pyrrolo, and tetrahydrothiophen-yl.

The abbreviation "Ar" stands for an aryl group. Aryl groups which can be used with present invention include phenyl, substituted phenyl, as defined above, heteroaryl, and substituted heteroaryl. The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino groups.

The term "$C_7$ to $C_{12}$ phenylalkyl" denotes a $C_1$ to $C_6$ alkyl group substituted at any position by a phenyl ring. Examples of such a group include benzyl, 2-phenylethyl, 3-phenyl (n-propyl), 4-phenylhexyl, 3-phenyl(n-amyl), 3-phenyl(sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, (monosubstituted) amino, protected (monosubstituted)amino, (disubstituted) amino, guanidino, heterocyclic ring, substituted heterocyclic ring, $C_1$ to $C_7$ alkoxy, $C_1$ to $C_7$ substituted alkoxy, $C_1$ to $C_7$ acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-$C_1$ to $C_6$ alkyl) carboxamide, N,N-($C_1$ to $C_6$dialkyl)carboxamide, cyano, N-(($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino, cyclic $C_2$ to $C_7$ alkylene or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "phenoxy" denotes a phenyl bonded to an oxygen atom provided that the phenoxy is bonded to the quinoline ring through the oxygen atom as opposed to a carbon atom of the phenyl ring. The term "substituted phenoxy" specifies a phenoxy group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino and N-(phenylsulfonyl)amino.

Examples of substituted phenoxy include 2-methylphenoxy, 2-ethylphenoxy, 2-propylphenoxy, 2-isopropylphenoxy, 2-sec-butylphenoxy, 2-tert-butylphenoxy, 2-allylphenoxy, 2-propenylphenoxy, 2-cyclopentylphenoxy, 2-fluorophenoxy, 2-(trifluoromethyl) phenoxy, 2-chlorophenoxy, 2-bromophenoxy, 2-methoxyphenoxy, 2-ethoxyphenoxy, 2-isopropoxyphenoxy, 3-methylphenoxy, 3-ethylphenoxy, 3-isopropylphenoxy, 3-tert-butylphenoxy, 3-pentadecylphenoxy, 3-(trifluoromethyl)phenoxy, 3-fluorophenoxy, 3-chlorophenoxy, 3-bromophenoxy, 3-iodophenoxy, 3-methoxyphenoxy, 3-(trifluoromethoxy) phenoxy, 4-methylphenoxy, 4-ethylphenoxy, 4-propylphenoxy, 4-isopropylphenoxy, 4-sec-butylphenoxy, 4-tert-butylphenoxy, 4-tert-amylphenoxy, 4-nonylphenoxy, 4-dodecylphenoxy, 4-cyclopenylphenoxy, 4-(trifluoromethyl)phenoxy, 4-fluorophenoxy, 4-chlorophenoxy, 4-bromophenoxy4-iodophenoxy, 4-methoxyphenoxy, 4-(trifluoromethoxy)phenoxy, 4-ethoxyphenoxy, 4-propoxyphenoxy, 4-butoxyphenoxy, 4-hexyloxyphenoxy, 4-heptyloxyphenoxy, 2,3-dimethylphenoxy, 5,6,7,8-tetrahydro-1-naphthoxy, 2,3-dichlorophenoxy, 2,3-dihydro-2,2-dimethyl-7-benzofuranoxy, 2,3-dimethoxyphenoxy, 2,6-dimethylphenoxy, 2,6-diisopropylphenoxy, 2,6-di-sec-butylphenoxy, 2-tert-butyl-6-methylphenoxy, 2,6-di-tert-butylphenoxy, 2-allyl-6-methylphenoxy, 2,6-difluorophenoxy, 2,3-difluorophenoxy, 2,6-dichlorophenoxy, 2,6-dibromophenoxy, 2-fluoro-6-methoxyphenoxy, 2,6-dimethoxyphenoxy, 3,5-dimethylphenoxy, 5-isopropyl-3-methylphenoxy, 3,5-di-tert-butylphenoxy, 3,5-bis(trifluoromethyl)phenoxy, 3,5-difluorophenoxy, 3,5-dichlorophenoxy, 3,5-dimethoxyphenoxy, 3-chloro-5-methoxyphenoxy, 3,4-dimethylphenoxy, 5-indanoxy, 5,6,7,8-tetrahydro-2-naphthoxy, 4-chloro-3-methylphenoxy, 2,4-dimethylphenoxy, 2,5-dimethylphenoxy, 2-isopropyl-5-methylphenoxy, 4-isopropyl-3-methylphenoxy, 5-isopropyl-2-methylphenoxy, 2-tert-butyl-5-methylphenoxy, 2-tert-butyl-4-methylphenoxy, 2,4-di-tert-butylphenoxy, 2,4-di-tert-amylphenoxy, 4-fluoro-2-methylphenoxy, 4-fluoro-3-methylphenoxy, 2-chloro-4-methylphenoxy, 2-chloro-5-methylphenoxy, 4-chloro-2-methylphenoxy, 4-chloro-3-ethylphenoxy, 2-bromo-4-methylphenoxy, 4-iodo-2-methylphenoxy, 2-chloro-5-(trifluoromethyl)phenoxy, 2,4-difluorophenoxy, 2,5-difluorophenoxy, 3,4-difluorophenoxy, 4-chloro-2-fluorophenoxy, 3-chloro-4-fluorophenoxy, 4-chloro-3-fluorophenoxy, 2-bromo-4-fluorophenoxy, 4-bromo-2-fluorophenoxy, 2-bromo-5-fluorophenoxy, 2,4-dichlorophenoxy, 3,4-dichlorophenoxy, 2,5-dichlorophenoxy, 2-bromo-4-chlorophenoxy, 2-chloro-4-fluorophenoxy, 4-bromo-2-chlorophenoxy, 2,4-dibromophenoxy, 2-methoxy-4-methylphenoxy, 4-allyl-2-methylphenoxy, trans-2-ethoxy-5-(1-propenyl)phenoxy, 2-methoxy-4-propenylphenoxy, 3,4-dimethoxyphenoxy, 3-ethoxy-4-methoxyphenoxy, 4-allyl-2,6-dimethoxyphenoxy, 3,4-methylenedioxyphenoxy, 2,3,6-trimethylphenoxy, 2,4-dichloro-3-methylphenoxy, 2,3,4-trifluorophenoxy, 2,3,6-trifluorophenoxy, 2,3,5-trifluorophenoxy, 2,3,4-trichlorophenoxy, 2,3,6-trichlorophenoxy, 2,3,5-trimethylphenoxy, 3,4,5-trimethylphenoxy, 4-chloro-3,5-dimethylphenoxy, 4-bromo-3,5-dimethylphenoxy, 2,4,6-trimethylphenoxy, 2,6-bis(hydroxymethyl)-4-methylphenoxy, 2,6-di-tert-butyl-4-methylphenoxy, 2,6-di-tert-butyl-4-methoxyphenoxy, 2,4,5-trifluorophenoxy, 2-chloro-3,5-difluorophenoxy, 2,4,6-trichlorophenoxy, 3,4,5-trimethoxyphenoxy, 2,3,5-trichlorophenoxy, 4-bromo-2,6-dimethylphenoxy, 4-bromo-6-chloro-2-methylphenoxy, 2,6-dibromo-4-methylphenoxy, 2,6-dichloro-4-fluorophenoxy, 2,6-dibromo-4-fluorophenoxy, 2,4,6-tribromophenoxy, 2,4,6-triiodophenoxy, 2-chloro-4,5-dimethylphenoxy, 4-chloro-2-isopropyl-5-methylphenoxy, 2-bromo-4,5-difluorophenoxy, 2,4,5-trichlorophenoxy, 2,3,5,6-tetrafluorophenoxy and the like.

The term "$C_7$ to $C_{12}$ phenylalkoxy" denotes a $C_7$ to $C_{12}$ phenylalkoxy group, provided that the phenylalkoxy is bonded to the quinoline ring through the oxygen atom. By "$C_7$ to $C_{12}$ substituted phenylalkoxy" is meant $C_7$ to $C_{12}$ phenylalkoxy group which can be substituted on the $C_1$ to $C_6$ alkyl portion with one or more, and preferably one or two, groups chosen from halogen, hydroxy, protected hydroxy, oxo, protected oxo, amino, protected amino, (monosubstituted)amino, protected (monosubstituted) amino, (disubstituted)amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-$C_1$ to $C_6$ alkyl) carboxamide, N,N-($C_1$ to $C_6$ dialkyl)carboxamide, cyano, N-(($C_1$ to $C_6$ alkylsulfonyl)amino, thiol, $C_1$ to $C_4$ alkylthio, $C_1$ to $C_4$ alkylsulfonyl groups; and/or the phenyl group can be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl) carboxamide, trifluoromethyl, N-(($C_1$ to $C_6$ alkyl)sulfonyl) amino, N-(phenylsulfonyl)amino or a phenyl group, substituted or unsubstituted, for a resulting biphenyl group. The substituted alkyl or phenyl groups may be substituted with one or more, and preferably one or two, substituents which can be the same or different Examples of the term "$C_7$ to $C_{12}$ substituted phenylalkoxy" include groups such as 2-(4-hydroxyphenyl)ethoxy, 4-(4-methoxyphenyl)butoxy, (2R)-3-phenyl-2-aminopropoxy, (2S)-3-phenyl-2-amino-propoxy, 2-indanoxy, 6-phenyl-1-hexanoxy, cinnamyloxy, (±)-2-phenyl-1-propoxy, 2,2-dimethyl-3-phenyl-1-propoxy and the like.

The term "phthalimide" means a cyclic imide which is made from phthalic acid, also called 1, 2 benezenedicarboxylic acid. The term "substituted phthalimide" specifies a phthalimide group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino and N-(phenylsulfonyl)amino.

Examples of substituted phthalimides include 4,5-dichlorophthalimido, 3-fluorophthalimido, 4-methoxyphthalimido, 3-methylphthalimido, 4-carboxyphthalimido and the like.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino.

Examples of the term "substituted naphthyl" includes a mono or di(halo)naphthyl group such as 1, 2, 3, 4, 5, 6, 7 or 8-chloronaphthyl, 2, 6-dichloronaphthyl, 2, 5-dichloronaphthyl, 3, 4-dichloronaphthyl, 1, 2, 3, 4, 5, 6, 7 or 8-bromonaphthyl, 3, 4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2, 4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1, 2, 4-dimethylnaphthyl, 1, 2, 3, 4, 5, 6, 7 or 8-(isopropyl) naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy)naphthyl group, for example, 2, 6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy)naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2, 4-di(-protected carboxy)naphthyl; a mono-or di(hydroxymethyl)naphthyl or (protected hydroxymethyl) naphthyl such as 1, 2, 3, 4, 5, 6, 7 or 8-(protected hydroxymethyl)naphthyl or 3, 4-di(hydroxymethyl) naphthyl; a mono- or di(amino)naphthyl or (protected amino)naphthyl such as 1, 2, 3, 4, 5, 6, 7 or 8-(amino) naphthyl or 2, 4-(protected amino)-naphthyl, a mono- or di(aminomethyl)naphthyl or (protected aminomethyl) naphthyl such as 2, 3, or 4-(aminomethyl)naphthyl or 2, 4-(protected aminomethyl)naphthyl; or a mono- or di-(N-methylsulfonylamino)naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The terms "halo" and "halogen" refer to the fluoro, chloro, bromo or iodo groups. There can be one or more halogen, which are the same or different. Preferred halogens are chloro and fluoro.

The term "(monosubstituted)amino" refers to an amino group with one substituent chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl and heterocyclic ring. The (monosubstituted)amino can additionally have an amino-protecting group as encompassed by the term "protected (monosubstituted)amino".

The term "(disubstituted)amino" refers to amino groups with two substituents chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-l-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy) benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydoxymethyl" which refer to a hydroxy or hydroxymethyl substituted with one of the above hydroxy-protecting groups.

The substituent term "$C_1$ to $C_4$ alkylthio" refers to sulfide groups such as methylthio, ethylthio, n-propylthio, isopropylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "$C_1$ to $C_4$ alkylsulfonyl" encompasses groups such as methylsulfonyl, ethylsulfonyl, n-propylsulfonyl, isopropylsulfonyl, n-butylsulfonyl, t-butylsulfonyl and the like.

The terms "$C_1$ to $C_4$ substituted alkylthio," "$C_1$ to $C_4$ substituted alkylsulfoxide," and "$C_1$ to $C_4$ substituted alkylsulfonyl," denote the $C_1$ to $C_4$ alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "$C_1$ to $C_6$ alkylaminocarbonyl" means a $C_1$ to $C_6$ alkyl attached to an aminocarbonyl group, where the $C_1$ to $C_6$ alkylaminocarbonyl groups are the resulting urea when an isocyanate is used in the reaction scheme. Examples of $C_1$ to $C_6$ alkylaminocarbonyl include methylaminocarbonyl (from methylisocyanate), ethylaminocarbonyl (from ethylisocyanate), propylaminocarbonyl (from propylisocyanate), butylaminocarbonyl (from butylisocyatate). The term "$C_1$ to $C_6$ substituted alkylaminocarbonyl" denotes a substituted alkyl bonded to an aminocarbonyl group, which alkyl may be substituted as described above in relation to $C_1$ to $C_6$ substituted alkyl. Examples of $C_1$ to $C_6$ substituted alkylaminocarbonyl include, for example, methoxymethylaminocarbonyl (from methoxymethylisocyanate), 2-chloroethylaminocarbonyl (from 2-chloroethylisocyanate), 2-oxopropylaminocarbonyl (from 2-oxopropylisocyanate), and 4-phenylbutylaminocarbonyl (from phenylbutylisocyanate).

The term "phenylaminocarbonyl" means a phenyl attached to an aminocarbonyl group, where the phenylaminocarbonyl groups are the result of using a phenylisocyanate in the reaction scheme. The term "substituted phenylaminocarbonyl" denotes a substituted phenyl bonded to an aminocarbonyl group, which phenyl may be substituted as described above in relation to substituted phenyl. Examples of substituted phenylaminocarbonyl include 2-chlorophenylaminocarbonyl (from 2-chlorophenylisocyanate), 3-chlorophenylaminocarbonyl (from 3-chlorophenylisocyanate), 2-nitorphenylaminocarbonyl (from 2-nitrophenylisocyanate) 4-biphenylaminocarbonyl (from 4-biphenylisocyanate), and 4-methoxyphenylaminocarbonyl (from 4-methoxyphenylisocyanate).

The substituent terms "cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ to $C_7$ heteroalkylene.

The cyclic alkylene or heteroalkylene group may be substituted once or twice by the same or different substituents selected from the group consisting of the following moieties: hydroxy, protected hydroxy, carboxy, protected carboxy, oxo, protected oxo, $C_1$ to $C_4$ acyloxy, formyl, $C_1$ to $C_7$ acyl, $C_1$ to $C_6$ alkyl, $C_1$ to $C_7$ alkoxy, $C_1$ to $C_4$ alkylthio, $C_1$ to $C_4$ alkylsulfoxide, $C_1$ to $C_4$ alkylsulfonyl, halo, amino, protected amino, (monosubstituted)amino, protected (monosubstituted)amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydroindanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the phenyl is fused to a pyridino, pyrano, pyrrolo, pyridinyl, dihydropyrrolo, or dihydropyridinyl ring. Examples of fused cyclic groups which each contain one oxygen atom and one or two double bonds are when the phenyl ring is fused to a furo, pyrano, dihydrofurano, or dihydropyrano ring. Examples of fused cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

One or more of the tetrahydro-quinoline derivatives, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., *J. Pharm. Sci.*, 66:1–19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_3$ is substituted with a (quaternary ammonium) methyl group. A preferred cation for the carboxylate anion is the sodium cation.

The compounds of the above Formulae can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more tetrahydro-quinoline derivatives, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the α-($C_1$ to $C_7$) alkoxyethyl groups, for example methoxyethyl, ethoxyethyl, propoxyethyl, isopropoxyethyl and the like; the 2-oxo-1,3-dioxlen-4-ylmethyl groups, such as 5-methyl-2-oxo-1,3-dioxolen-4-ylmethyl, 5-phenyl-2-oxo-1,3-dioxolen-4-ylmethyl and the like; the $C_1$ to $C_4$ alkylthiomethyl groups, for example methylthiomethyl, ethylthiomethyl, isopropylthiomethyl and the like; the acyloxymethyl groups, for example pivaloyloxymethyl, pivaloyloxyethyl, α-acetoxymethyl and the like; the ethoxycarbonyl-1-methyl group; the α-acetoxyethyl; the 1-($C_1$ to $C_7$ alkyloxycarbonyloxy)ethyl groups such as the 1-(ethoxycarbonyloxy)ethyl group; and the 1-($C_1$ to $C_7$ alkylaminocarbonyloxy)ethyl groups such as the 1-(methylaminocarbonyloxy)ethyl group.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), β-Alanine, L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration or the D-amino acid can readily be substituted for that in the L-configuration.

The compounds of Formula I and combinatorial libraries containing the same can be prepared as set forth in the Reaction Schemes provided in the Figures and described below. The substituents $R^1$ to $R^8$ in the Reaction Schemes have the same meaning as those described above. The substituent Y in the Reaction Schemes is the same as defined above with the exception that it is still bound to resin or is the functionalized resin and, therefore, has one less hydrogen.

In brief, the tetrahydro-quinoline compounds of the present invention can be prepared according to Reaction Scheme I as shown in FIG. 1. As depicted in FIG. 1, a solid support resin-bound amine (1) (resin identified by Ⓡ) is reacted, in situ, with an aldehyde (2) and, thereby, converted to the corresponding imine (3). In the presence of base, addition of an acid halide, such as methoxyacetyl chloride, yields the beta lactam (4). Reduction of the nitro group leads to rearrangement of the beta-lactam, producing the tetrahydroquinoline (5).

Figure 2:
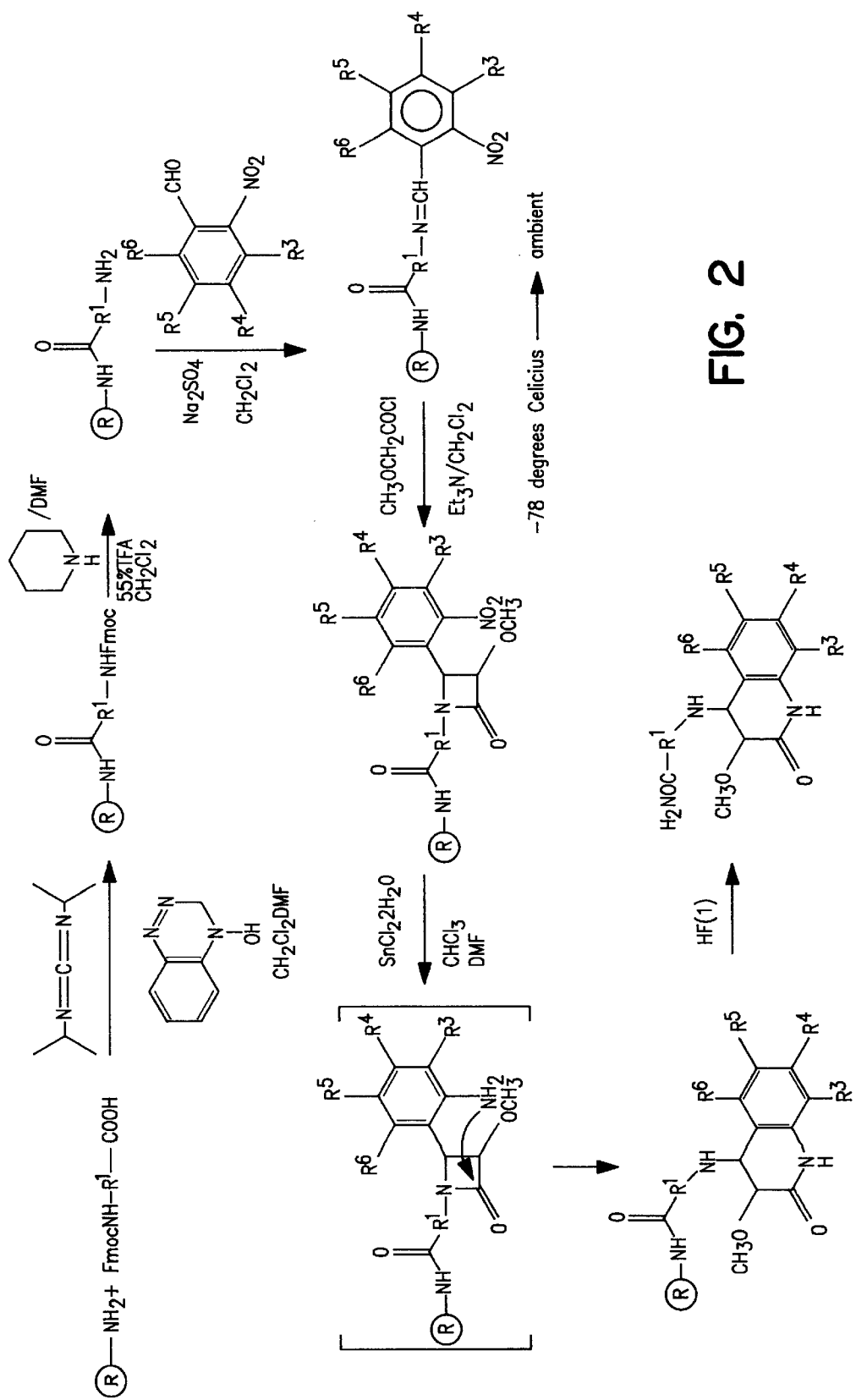
FIG. 2 shows a more detailed reaction scheme, Reaction Scheme II, for the preparation of the subject tetrahydro-quinolines and libraries containing the same.

More specifically, as shown by Reaction Scheme II in FIG. 2, preparation of the tetrahydroquinolines and libraries containing the same are prepared by the following more detailed steps. First, diverse amino carboxylic acids which are amino-protected with, for example, Fmoc (as shown in FIG. 2), Boc and the like, are coupled to resin, such as MBHA (FIG. 2), MBA, Tentagel™ and the like as described below, using a carbodiimide coupling agent, such as dicyclohexylcarbodiimide, diisopropylcarbodiimide, N-dimethylaminoethyl-N'-ethyl-carbodiimide and the like, and an activator, such as 1-hydroxybenzotriazole, 7-aza-1-hydroxybenzotriazole and the like, in an aprotic polar solvent such as dichloromethane, dimethylformamide and the like, at between 10° C. and 100° C., preferably at 25° C., for 2 to 24 hours, preferably 8 to 16 hours. Thereafter, the amino carboxylic acid is deprotected at the nitrogen with a secondary amine base using known conditions, such as piperidine (20% v/v) in dimethylformamide (for Fmoc) or trifluoroacetic acid (10–50% v/v) in dichloromethane (for Boc), for 5 to 60 minutes. Deprotection is followed by the free amino group being condensed with an aldehyde to the individual or mixtures of resin-bound amino carboxylic acids using, a drying reagent, such as magnesium sulfate or sodium sulfate, or an orthoformate, such as trimethyl or triethyl orthoformate, as a scavenger for water in a polar solvent, such as dichloromethane, dimethylformamide, dimethylacetamide, N-methylpyrrolidinone or the like, for a period of 1 to 72 hours, usually 12 to 24 hours at 20° C. to 75° C. and preferably at 25° C. Aldehyde condensation is followed by reaction under standard conditions with acid halide, in the case of Reaction Scheme II, methoxyacetyl chloride, and an amine base (e.g. a trialkylamine) under inert atmosphere ($N_2$) in an aprotic solvent such as dichloromethane, chloroform, dimethylformamide, dimethylacetamide, N-methylpyrrolidinone for 2 to 36 hours and preferably 16 hours at −78° C. to 125° C., preferably at −78° C. initially then allowing the temperature to warm to ambient temperature. The intermediate nitro substituted beta lactam is subjected to conditions to reduce the nitro group to an amine, in the case of Reaction Scheme II tin dichloride, in an aprotic solvent such as chloroform, dimethylformamide, dimethylacetamide, N-methylpyrrolidinone for 2 to 36 hours and preferably 16 hours at 20° C. to 125° C., preferably at 25°–30° C. to arrive at novel tetrahydroquinoline derivatives. Finally, the compounds can be cleaved from the resin by the methods common to those skilled in the art and the compounds tested for biological activity. It should be appreciated by those of skill in the art that with certain resins, cleavage from the resin results in the functional group on the resin coming off the resin and being maintained with the cleaved compounds. For example, with an amino-resin, such as methylbenzhydrylamine resin, the amine group from the resin is cleaved off the resin and makes the tetrahydro-quinoline(s) of interest an amide.

The term "functionalized resin" means any resin where functional groups have been introduced into the resin, as is common in the art. Such resins include, for example, those functionalized with amino, amide, or hydroxy groups. Such resins which can serve as solid supports are well known in the art and include, for example, 4-methylbenzhydrylamine-copoly(styrene-1% divinylbenzene) (MBHA), 4-hydroxymethylphenoxymethyl-copoly(styrene-1% divinylbenzene), 4-oxymethyl-phenylacetamido-copoly (styrene-1% divinylbenzene)(Wang), 4-(oxymethyl)-phenylacetamido methyl (Pam), and Tentagel™, from Rapp Polymere Gmbh, trialkoxy-diphenylmethyl ester-copoly (styrene-1% divinylbenzene)(RINK) all of which are commercially available. Preparation of the combinatorial libraries can be by the "split resin approach." The split resin approach is described by, for example, U.S. Pat. No. 5,010, 175 to Rutter, WO PCT 91/19735 to Simon, and Gallop et al., *J. Med. Chem.*, 37:1233–1251 (1994), all of which are incorporated herein by reference.

Exemplary amino carboxylic acids which can be used in the above Reaction Schemes include Nα-Boc-L-alanine, Nα-Boc-S-(Mob)-L-cysteine, Nα-Boc-L-aspartic acid-β-benzyl ester, Nα-Boc-L-glutamic acid-γ benzyl ester, Nα-Boc-L-phenylalanine, Nα-Boc-glycine, Nα-Boc-$N_{im}$-(Dnp)-L-histidine, Nα-Boc-L-isoleucine, Nα-Boc-L-lysine (2-Cl-Cbz), Nα-Boc-L-leucine, Nα-Boc-L-Cbz-methionine sulfoxide, Nα-Boc-L-asparagine, Nα-Boc-L-glutamine, Nα-Boc-L-serine(Bzl), Nα-Boc-L-threonine(Bzl) Nα-Boc-L-valine, Nα-Boc-L-tryptophan(CHO), Nα-Boc-L-tyrosine (2-Br-Cbz), Nα-Boc-D-alanine, Nα-Boc-S-(Mob)-D-cysteine, Nα-Boc-D-aspartic acid-β benzyl ester, Nα-Boc-D-glutamic acid-γ-benzyl ester, Nα-Boc-D-phenylalanine, Nα-Boc-D-isoleucine, Nα-Boc-D-lysine(2-Cl-Cbz), Nα-Boc-D-leucine, Nα-Boc-D-methionine, Nα-Boc-D-asparagine, Nα-Boc-D-glutamine, Nα-Boc-D-serine(Bzl), Nα-Boc-D-threonine(Bzl), Nα-Boc-D-valine, Nα-Boc-D-tryptophan(CHO), Nα-Boc-D-tyrosine(2-Br-Cbz), Nα-Boc-L-norvaline, Nα-Boc-L-norleucine, Nα-Boc-L-phenylglycine, Nα-Boc-L-(2-naphthyl)alanine, Nα-Boc-L-cyclohexylalanine, Nα-Boc-Nε-Fmoc-L-lysine, Nα-Boc-L-(p-nitro)-phenylalanine, Nα-Boc-L-(p-chloro)-phenylalanine, Nα-Boc-L-(p-fluoro)-phenylalanine, Nα-Boc-L-(p-Fmoc-amino)-phenylalanine, Nα-Boc-L-(3-pyridyl)-alanine, Nα-Boc-L-(2-thienyl)-alanine, Nα-Boc-L-(O-ethyl)-tyrosine, Nα-Boc-aminoisobutyric acid, Nα-Boc-L-γ-aminobutyric acid, Nα-Boc-β-alanine, N-Boc-piperidine-4-carboxylic acid, N-Boc-6-aminohexanoic acid, Nα-Boc-β-fluorenylmethyl-L-aspartic acid, Nα-Boc-L-glutamic acid-α-benzyl ester, Nα-Boc-L-3,4-dehydroproline, Nα-Boc-L-isoasparagine, Nα-Boc-L-hydroxyproline(O-Bzl), Nα-Boc-Nδ-Cbz-L-ornithine, Nα-Boc-L-methionine sulfone, Nδ-Boc-Nα-Cbz-L-ornithine, Nε-Boc-Nα-Cbz-L-lysine, Nα-Boc-L-thioproline, Nα-Boc-L-γ-aminobutyric acid, 3R,4S-Nα-Boc-phenylstatin, Nα-Boc-L-(p-benzoyl)-phenylalanine, Nα-Boc-Nε-acetyl-L-lysine, Nα-Boc-L-homoproline, N-Boc-octahydro-indole-2-carboxylic acid, N-Boc-7-aminoheptanoic acid, Nα-Boc-L-(4-iodo)-phenylalanine, Nα-Boc-L-isoglutamine, Nα-Boc-L-cyclohexylglycine, Nα-Boc-L-aspartic acid-α-benzyl ester, 4-aminohippuric acid, Nα-Boc-L-t-butylglycine, Nα-Boc-L-aspartic acid-α-benzyl ester, Nα-Boc-L-aspartic acid-α-fluoromethyl ester, Nα-Boc-Nδ-Fmoc-L-ornithine, Nα-Boc-glutamic acid (OFm), Nα-Boc-L-1,2,3,4-tetrahydroisoquinoline-3-carboxylic acid, Nα-Boc-L-tyrosine(O-(2,6 dichlorobenzyl)), N-Boc-L-7-hydroxy-1,2,3,4-tetrahydroisoquinoline-3-carboxylic acid, Nα-Boc-D-norvaline, Nα-Boc-D-norleucine, Nα-Boc-D-phenylglycine, Nα-Boc-D-3-(2-naphthyl)alanine, Nα-Boc-D-cyclohexylalanine, Nα-Boc-Nε-Fmoc-D-lysine, Nα-Boc-D-(4-nitro)-phenylalanine, Nα-Boc-D-(4-chloro)-phenylalanine, Nα-Boc-D-(4-fluoro)-phenylalanine, Nα-Boc-D-(N-Fmoc-amino)-phenylalanine, Nα-Boc-D-(3-pyridyl)-alanine, Nα-Boc-(2-thienyl)-D-alanine, Nα-Boc-D-tyrosine(O-ethyl), Nα-Boc-D-1,2,3,4-tetrahydroisoquinoline-3-carboxylic acid, Nα-Boc-D-Tyrosine(O-(2,6-dichlorobenzyl)), N-Boc-D-7-hydroxy-1,2,3,4-tetrahydroisoquinoline-3-carboxylic acid, Nα-Boc-D-citrulline, 3R-4S-Nα-Boc-statine, Nα-Boc-S-(acetamidomethyl)-D-cysteine, Nα-Boc-N$_{im}$-Boc-D-histidine, Nα-Boc-D-tryptophan, Nα-Boc-Nε-(3,4-dichlorobenzyl)-D-lysine, Nα-Boc-Nα-methyl-L-leucine, Nα-Boc-Nα-methyl-L-phenylalanine, Nα-Boc-Nα-methyl-L-alanine, Nα-Boc-Nα-methyl-L-valine, Nα-Boc-Nα-methyl-L-tyrosine(O-(2,6-dichlorobenzyl)), Nα-Boc-Nα-methyl-arginine(Tos), Nα-Boc-sarcosine, 2-aminoethanoic acid, 3-aminopropionic acid, 4-(N-Boc-aminomethyl) benzoic acid, aminoheptanoic acid, 5-aminopentanoic acid, (S)-2,3-diaminopropanoic acid, (S)-2,6-diaminohexanoic acid, (S)-3-amino-2-methylpropionic acid, (R)-3-amino-2-methylpropionic acid, 2-(2-aminoethoxyethoxy)acetic acid and trans-4-(aminomethyl)cyclohexanecarboxylic acid. Additional amino carboxylic acids are provided in the ensuing Examples.

Exemplary aldehydes which can be used in the above Reaction Schemes I and II are 2-nitrobenzaldehyde, 2,4-dinitrobenzaldehyde, 4-methyl-2-nitrobenzaldehyde, 4,5-methylenedioxy-2-nitrobenzaldehyde, 5-ethyl-2-nitrobenzaldehyde, 4,5-dimethoxy-2-nitrobenzaldehyde, 5-chloro-2-nitrobenzaldehyde, 3-fluoro-2-nitrobenzaldehyde, 3-trifluoro-2-nitrobenzaldehyde, 4-(dimethylamino)-2-nitrobenzaldehyde, 3-methoxy-2-nitrobenzaldehyde, 5-hydroxy-2-nitrobenzaldehyde, 2,6-dinitrobenzaldehyde and the like.

Exemplary acid halides which can be used in the above Reaction Schemes ($R^2$—$CH_2$—$C(O)$—$X_1$) include, but are not limited to, methoxyacetyl chloride, phenoxyacetyl chloride, 4-chlorophenoxyacetyl chloride benzyloxyacetyl chloride and acetoxyacetyl chloride. The only requirement is that the acid halide have at least one hydrogen alpha to the carbonyl.

The tetrahydro-quinolines prepared by the above Reaction Schemes, once cleaved from the resin, result in compounds of Formula II:

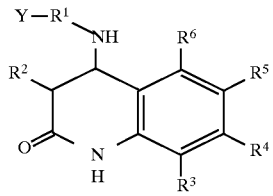

FORMULA II

These tetrahydroquinoline compounds of Formula II can be converted, generally before cleavage from the resin, to alternatively substituted compounds having an alkyl or acyl, or other functionality as defined by $R^7$ and/or $R^8$ above and provided by Formula I:

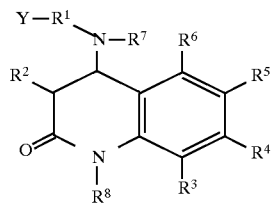

FORMULA I

Figure 3:
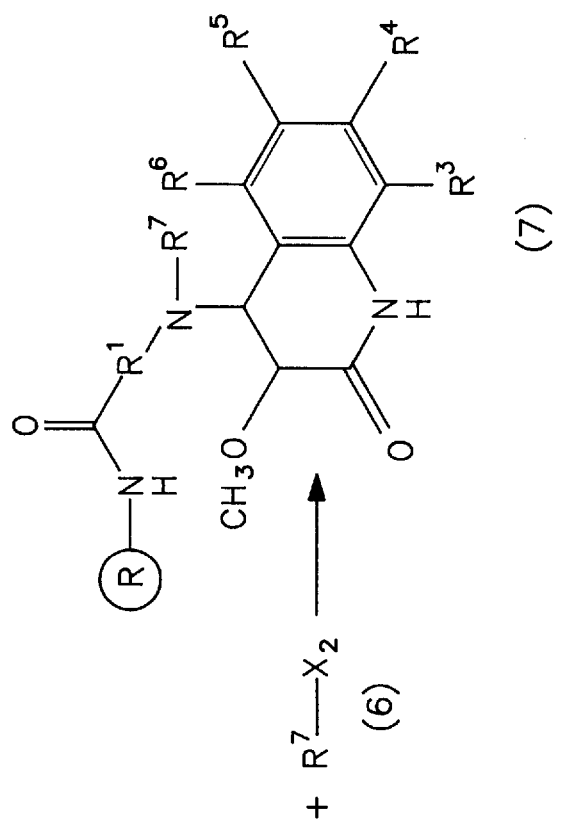
FIG. 3 provides Reaction Scheme III for the preparation of libraries and compounds containing alternatively substituted tetrahydro-quinolines at the $R^7$ and/or $R^8$ position(s).
Figure 3:
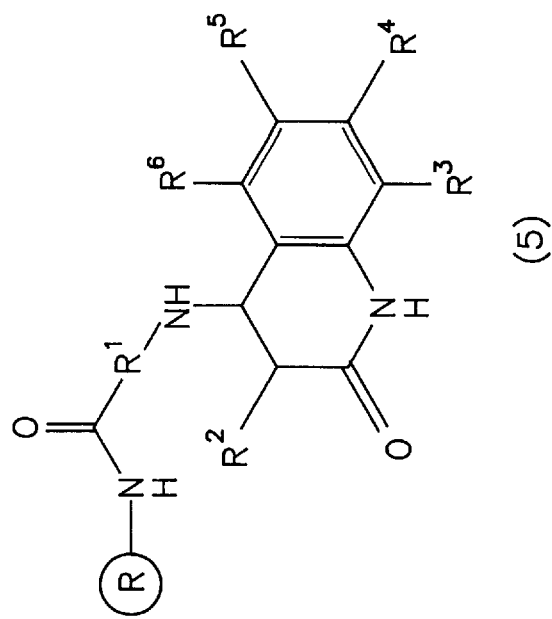

The tetrahydro-quinolines of Formula II, before cleavage from the resin, can be substituted at positions $R^7$ and/or $R^8$ following Reaction Scheme III provided in FIG. 3. Briefly, as shown in Reaction Scheme III, the tetrahydro-quinoline (5) prepared by the above Reaction Schemes I or II is condensed with a carboxylic acid, carboxylic acid anhydride, acid halide, alkyl halide or isocyanate (6) in an aprotic solvent, such as dimethylformamide, dichloromethane, 1-methyl-2- pyrrolidinone, N-N,-dimethylacetamide, tetrahydrofuran, dioxane and the like, in the presence of an acid acceptor to furnish the substituted tetrahydro-quinoline (7).

For example, preparation of the library containing alternatively substituted tetrahydro-quinolines other than $R^7$ equal to a hydrogen atom involves, instead of cleaving from the resin, free NH of the newly formed tetrahydro-quinoline compound being reacted with a carboxylic acid activated with N-[(dimethylamino)-1H-1,2,3-triazolo[4,5-b]pyridin-1-ylmethylene]-N-methylmethanaminium hexafluorophosphate N-oxide (HATU, PerSeptive Biosystems, Farmingham, Mass.), dissolved in dimethylformamide, N-N,-dimethylacetamide, 1-methyl-2-pyrrolidinone and the like. The reaction is allowed to proceed for 1 to 24 hours at 20° C. to 80° C., preferably at 25° C. for 3 to 5 hours to yield various carboxamide derivatives. Finally, the compounds are cleaved from the resin as described above and tested for biological activity.

Exemplary carboxylic acid, carboxylic acid anhydride, acid halide, alkyl halide or isocyanate (6) which can be used include nalidixic acid,2-phenyl-4-quinolinecarboxylic acid, 2-pyrazinecarboxylic acid, niflumic acid, 4-nitrophenylacetic acid, 4-(-nitrophenyl)butyric acid, (3,4-dimethoxyphenyl)acetic acid, 3,4-(methylenedioxy) phenylacetic acid, 4-nitrocinnamic acid, 3,4,-(methylenedioxy)cinnamic acid, 3,4,5-trimethoxycinnamic acid, benzoic acid, 2-chlorobenzoic acid, 2-nitrobenzoic acid, 2-(p-toluoyl)benzoic acid, 2,4-dinitrophenylacetic acid, 3-(3,4,5-trimethoxyphenyl)-proprionic acid, 4-biphenylacetic acid, 1-napthylacetic acid, (2-napthoxy) acetic acid, trans-cinnamic acid, picolinic acid, 3-amino-4-hydroxybenzoic acid, (4-pyridylthio)acetic acid, 2,4-dichlorobenzoic acid, 3,4-dichlorobenzoic acid, 4-biphenylcarboxylic acid, thiophenoxyacetic acid, 1-benzoylpropionic acid, phenylacetic acid, hydrocinnamic acid, 3,3-diphenylpropionic acid, 3,3,3-triphenylpropionic acid, 4-phenylbutyric acid, phenoxyacetic acid, (±)-2-phenoxypropionic acid, 2,4-dimethoxybenzoic acid, 3,4-dimethoxybenzoic acid, 3,4-dihydroxybenzoic acid, 2,4-dihydroxybenzoic acid, 3,4,5-trimethoxybenzoic acid, 3,4,5-triethoxybenzoic acid, 3,4,5-trihydroxybenzoyl, 2-benzoylbenzoic acid, 1-napthoic acid, xanthene-9-carboxylic acid, 4-chloro-2-nitrobenzoic acid, 2-chloro-4-nitrobenzoic acid, 4-chloro-3-nitrobenzoic acid, 2-chloro-5-nitrobenzoic acid, 4-dimethylaminobenzoic acid, 4-(diethylamino)benzoic acid, 4-nitrobenzoic acid, 3-dimethylaminobenzoic acid, p-toluic acid, p-anisic acid, trimethylacetic acid, tert-butylacetic acid, (−)-menthoxyacetic acid, cyclohexanecarboxylic acid, cyclohexylacetic acid, dicyclohexylacetic acid, cyclohexanebutyric acid, cycloheptanecarboxylic acid, abietic acid, acetic acid, octanoic acid, (methylthio)acetic acid, 3-nitropropionic acid, 4-amino-3 hydroxybenzoic acid, 2-methyl-4-nitro-1-imidizole propionic acid, 2-furoic acid, (s)(-)-2-pyrrolidone-5-carboxylic acid, (2-pyrimidylthio) acetic acid, 4-methoxy-2-quinolinecarboxylic acid, 1-adamantanecarboxylic acid, piperonylic acid, 5-methyl-3-phenylisoxazole-4-carboxylic acid, 15 rhodanine-3-acetic acid, 2-norbornaneacetic acid, nicotinnic acid, 9-oxo-9H-thioxanthene-3-carboxylic acid 10,10 dioxide, 2-thiophenecarboxylic acid, 5-nitro-2-furoic acid, indole-3-acetic acid, isonicotinic acid, lithocholic acid, cholic acid, deoxycholic acid, hyodeoxycholic acid, Boc-L-Ala, Boc-L-Cys(Mob), Boc-L-Asp(Bzl), Boc-L-Glu(Bzl), Boc-L-Phe, Boc-Gly, Boc-L-His(Tos), Boc-L-Ile, Boc-L-Lys(Clz), Boc-L-Leu, Boc-Met(O), Boc-L-Asn, Boc-L-Pro, Boc-L-Gln, Boc-L-Arg(Tos), Boc-L-Ser(Bzl), Boc-L-Thr(Bzl), Boc-L-Val, Boc-L-Trp, Boc-L-Tyr(Brz), Boc-D-Ala, Boc-D-Cys (Mob), Boc-D-Asp(Bzl), Boc-D-Glu(Bzl), Boc-D-Phe, Boc-D-His(Dnp), Boc-D-Ile, Boc-D-Lys(Clz), Boc-D-Leu, Boc-D-Met(O), Boc-D-Asn, Boc-D-Pro, Boc-D-Gln, Boc-D-Arg(Tos), Boc-D-Ser(Bzl), Boc-D-Thr(Bzl), Boc-D-Val, Boc-D-Trp(CHO), Boc-D-Tyr(Brz), Boc-L-Met, 2-aminobutyric acid, 4-aminobutyric acid, 2-aminoisobutyric acid, L-norleucine, D-norleucine, 6-aminocaproic acid, 7-aminoheptanoic acid, thioproline, L-Norvaline, D-Norvaline, a-ornithine, methionyl sulfonyl, L-naphthyalanine, D-naphthyalanine, L-phenylglycine, D-phenylglycine, β-alanine, L-cyclohexylalanine, D-cyclohexylalanine, hydroxyproline, nitrophenylalanine, dehydroproline, 1,3-propane sultone, 1-propanesulfonyl chloride, 1-octanesulfonyl chloride, perfluoro-1-octanesulfonly fluoride, (+)-10-camphorsulfonyl chloride, (-)-10-camphorsulfonyl chloride, benzenesulfonly chloride, 2-nitrobenzenesulfonyl chloride, p-toluenesulfonyl chloride, 4-nitrobenzenesulfonyl chloride, n-acetylsulfanilyl chloride, 2,5-dichlorobenzenesulfonyl chloride, 2,4-dinitrobenzenesulfonyl chloride, 2-mesitylenesulfonyl chloride, 2-napthalenesulfonyl chloride, phenylisocyanate, methylisocyanate and t-butyl isocyanate. Those abbreviations used above for amino acids and their protecting groups are ones commonly used in the field, each of which are identified, for example, in Stewart and Young, supra.

Although Reaction Scheme III only shows, and the above description relates only to, the addition of $R^7$, it should be appreciated that $R^8$ can, under the same conditions, be similarly substituted. The nitrogen substituted with $R^7$ is more nucleophilic than the ring nitrogen and, therefore, can be substituted to the exclusion of $R^8$ or with only partial $R^8$ substitution. To obtain substitution at one position to the exclusion of another, such as at $R^8$ only, protection and deprotection schemes known in the art can be used.

Pharmaceutical compositions containing the new tetrahydro-quinoline derivatives are also included within the scope of the present invention; as are methods of using the compounds and compositions. The new tetrahydro-quinoline compounds of the present invention can be used for a variety of purposes and indications. For example, to evaluate whether the subject tetrahydro-quinolines have antimicrobial activity, and, therefore, can be used to treat infections, the ability of the compounds to inhibit bacterial growth can be determined by methods well known in the art. An exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5\times10^5$ colony-forming units/ml). The concentration of cells is established by plating 100 μl of the culture solution using serial dilutions (e.g., $10^{-2}$, $10^{-3}$ and $10^{-4}$) onto solid agar plates. In 96-well tissue culture plates tetrahydro-quinolines, individual or in mixtures, are added to the bacterial suspension at concentrations derived from serial two-fold dilutions ranging from 1500 to 2.9 μg/ml. The plates are incubated overnight at 37° C. and the growth determined at each concentration by $OD_{620}$ nm. The $IC_{50}$ (the concentration necessary to inhibit 50% of the growth of the bacteria) can then be calculated.

Additional assays can be used to test the biological activity of the instant tetrahydro-quinolines. Such as a competitive enzyme-linked immunoabsorbent assay and radio-receptor assays, both as described in greater detail below. The latter test, the radio-receptor assay, can be selective for either the μ, δ or κ opiate receptors and is therefore an indication of tetrahydro-quinolines' analgesic properties.

Competitive Enzyme-Linked Immunosorbent Assay (ELISA): The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 μl. After blocking, 25 μl of a 1.0 mg/ml solution of each tetrahydro-quinoline mixture of a synthetic combinatorial library (or individual tetrahydro-quinoline) is added, followed by MAb 125-10F3 (Appel et al., supra) (25 μl per well). The MAb is added at a fixed dilution in which the tetrahydro-quinoline in solution effectively competes for MAb binding with the antigenic peptide adsorbed to the plate. The remaining steps are the same as for direct ELISA. The concentration of tetrahydro-quinoline necessary to inhibit 50% of the MAb binding to the control peptide on the plate ($IC_{50}$) is determined by serial dilutions of the tetrahydro-quinoline.

Radio-Receptor Assay: Particulate membranes can be prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall® RC5C SA-600: Du Pont, Wilmington, Del.) (16,000 rpm) for 10 mins. The pellets are resuspended in fresh Tris-HCl buffer and incubated at 37° C. for 40 mins. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in M.M. Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 μg/ml of tetrahydro-quinoline, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the tetrahydro-quinolines, individually or in mixtures. $IC_{50}$ values (the concentration necessary to inhibit 50% of $^3$H-DAMGO binding) are then calculated. As opposed to this μ receptor selective assay, assays selective for δ receptors can be carried out using [$^3$H]-Naltrindole (3 nM, specific activity 32 Ci/mmol as radioligand or, alternatively, assays selective for κ receptors can be carried out using [$^3$H]-U69,593 (3 nM, specific activity 62 Ci/mmol) as radioligand.

As shown in the ensuing Examples 41 and 42, some of the subject compounds bind to certain opioid receptor subtypes. Because some of the compounds of the present invention bind to the μ or κ receptors, they can be used in in vitro assays to study the opiate receptor subtypes. For example, in a sample receptor of unknown type or origin, the compounds, after being labeled with a detectable marker such as a radioisotope, can be contacted with the receptor sample under conditions which specifically favor binding to a particular receptor subtype. Unbound receptor and compound can be removed, for example, by washing with a saline solution, and bound receptor can then be detected using methods well known to those skilled in the art. Therefore, the compounds of the present invention are useful in vitro for the diagnosis of relevant opioid receptor subtypes, and in particular the μ or κ types, in brains and other tissue samples.

In addition to their utility in in vitro screening methods, the compounds are also useful in vivo. For example, certain of the instant compounds can be used in vivo diagnostically to localize opioid receptor subtypes. The compounds are also useful as drugs to treat pathologies associated with other compounds which interact with the opioid receptor system. It can be envisioned that these compounds can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching).

As pharmaceutical compositions for treating infections, pain, or any other indication the tetrahydro-quinoline compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active tetrahydro-quinoline. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

EXAMPLE 1

Combinatorial Library Of Tetrahydro-quinoline Derivatives

This Example provides a representative solid-phase combinatorial synthesis of a library which would contain approximately 210 derivatives of tetrahydro-quinolines (THQs).

Following the above Reaction Scheme II, preparation of a library containing the THQs involves the following steps. Briefly, first, thirty five diverse amino carboxylic acid, varying at $R^1$, and including various amino-protected amino acids, are coupled to MBHA resin employing the tea-bag method of Houghten et. al, as described, for example in U.S. Pat. No. 4,631,211 to Houghten and Houghten et al., *Proc. Natl. Acad. Sci.*, 82:5131–5135 (1985), both of which are incorporated herein by reference. After coupling and thorough washing the 35 tea-bags, each containing one resin-bound amino carboxylic acid, are opened and the resin beads combined and thoroughly mixed as a suspension in dichloromethane (DCM). The resins are isolated by filtration and dried under vacuum, then divided into 6 equal portions and resealed in 6 labeled tea-bags, each tea-bag now having a mixture of the 35 amino carboxylic acids. This is followed by condensing 6 aldehydes, each differing by their $R^2$ substituent, using triethylorthoformate as dehydrating agent with the tea-bag contained mixtures of resin-bound amino carboxylic acids. One tea-bag, each containing the 35 resin-bound carboxylic acids, is used for each aldehyde in a separate reaction. After washing with an anhydrous solvent the tea-bags are collectively reacted with methoxyacetyl chloride and triethylamine in anhydrous dichloromethane (DCM). The intermediate lactam is treated with tin dichloride in DMF to reduce the nitro moiety and induce the ring opening rearrangement to arrive at a library of 210 derivatives of THQ. Finally, the mixtures are individually cleaved from the MBHA resin using a hydrogen fluoride (HF) procedure. The individual mixtures varying at $R^1$ and constant at $R^2$, each a mixture containing 35 individual compounds, can then be tested for biological activity using any one of a variety of screening assays, such as those described above or others well known in the art.

The individual amino carboxylic acids which can be used to prepare with a library of 210 THQs include the following: Ala, Arg, Asn, Asp, Cys, Gln, Glu, Gly, His, Ile, Leu, Lys, Met, Nva, Phe, Ser, Thr, Trp, Tyr, Val, D-Ala, D-Asp, D-Cys, D-Glu, D-Ile, D-Leu, D-Lys, D-Met, D-Phe, D-Ser, D-Thr, D-Tyr, and D-Val, β-alanine, and 4-aminobutyric acid. All are amino-protected with Fmoc or Boc and carry appropriate side chain protecting group as required. Individual aldehydes which can be employed are as follows: 2-nitrobenzaldehyde, 4,5-methylenedioxy-2-nitrobenzaldehyde, 4,5-dimethoxy-2-nitrobenzaldehyde, 5-chloro-2-nitrobenzaldehyde, 3-methoxy-2-nitrobenzaldehyde and 5-hydroxy-2-nitrobenzaldehyde.

1. Coupling of Amino Carboxylic Acids to MBHA Resin

Thirty five polypropylene mesh packets (T-bags, ~2" square, 65μ; McMaster Carr, Chicago, Ill.) of (0.6 g, 0.93 meq/g) MBHA resin are prepared, washed with DCM (2x, ~5 ml each), neutralized with 5% diisopropylethylamine/dichloromethane (DIEA/DCM) (3x, ~5 ml each), and washed with DCM (2x, ~5 ml each). Each resin packet is individually coupled overnight (~16 hrs except for Gly, 1 hr) by adding 10x amino acid in DCM (0.2M) or amino carboxylic acid in dimethylformamide (DMF) followed by 10x diisopropylcarbodiimide/DCM (0.2M) for a final reagent concentration of 0.1M (DMF, 5%) used to solubilize the Arg and Ser derivatives. Hydroxybenzotriazole (HOBt) (10x) is added to the amino carboxylic acids couplings. Following coupling completion, resin packets are washed with DCM (1x), isopropanol (IPA) (2x), and DCM (2x). Each packet is then opened and the resin carefully washed into a common vessel using alternating DCM and methanol (MeOH) washes (final volume, ~200 ml). The resin is mixed using a magnetic stir bar for 2.5 hrs. Resin is then filtered, washed with MeOH, and dried under vacuum. Based upon synthesis and cleavage of individual controls, reaction completion should be, and generally is, >95%.

2. Condensation of Benzaldehydes to the Mixture of a Resin-Bound Amino Carboxylic Acids Each packet is next shaken twice in 20% (v/v) piperidine/DMF (30 ml, 5 min, then 15 min) then washed with DMF (3x30 ml) and DCM (3x30 ml). A solution of the respective aldehyde (2 mmoles) and anhydrous trimethylorthoformate (0.438 ml, 4 mmoles) is prepared in DMF (7.5 ml) and added to the packet. After shaking for 3 hrs the packet is washed with dry (<0.03% water) DMF (5x30 ml).

3. Condensation with Methoxyacetyl Chloride and Reduction to Yield a Library of Tetrahydro-quinolines Each packet is then suspended in DCM (10 ml) and cooled to −78° C. Triethylamine (TEA) (0.42 ml, 3 mmoles) and a solution of methoxyacetyl chloride (0.18 ml, 2 mmoles) in DCM (5 ml) were added. After shaking the solution at −78° C. overnight, the reaction is allowed to warm to ambient temperature over 4 hrs, the packets are then washed with DCM, DMF and methanol (each 2x30 ml). All packets are collected in one bottle and shaken with 2M tin dichloride in DMF (80 ml) for 20 hrs, washed with DCM, DMF, and methanol (each 2x80 ml).

The tetrahydro-quinolines are cleaved off of the resin by treatment with HF (liquid (l)) at −15° C. for 2 hrs followed by warming to room temperature while removing HF (gaseous (g)) with a nitrogen stream. A scavenger, such as anisole, can be used where necessary.

EXAMPLE 2 TO EXAMPLE 4

4-[(N-Substituted)amino]-3,4-dihydro-3-(4-chlorophenoxy)-2(1H)-quinolinone

These examples provide the solid-phase synthesis of diastereoisomeric mixtures (approximately 1:1) of 4-(N-substituted)amino-3,4-dihydro-3-(4-chlorophenoxy)-2(1H)-quinolinone by condensing 2-nitrobenzaldehyde, 4-chlorophenoxyacetyl chloride and various amino acids on a polystyrene Wang resin. The quinolinones were cleaved from the solid support using 95% trifluoroacetic acid (TFA) in water.

1. Deprotection and Imine Formation

Fmoc-L-Ala-Wang-resin (Advanced ChemTech, lot # 14539, 0.72 mmol/g), Fmoc-Gly-Wang-resin (Advanced ChemTech, lot # 14963, 0.83 mmol/g) and Fmoc-L-Phe-Wang-resin (Advanced ChemTech, lot # 14413, 0.78 mmol/g) were placed separately in six porous polypropylene packets (2 packets/resin, 100 mg/packet). The packets were placed in a 60 ml polypropylene bottle and shaken with a solution of 20% piperidine in DMF (40 ml) at room temperature for 2 hrs. The liquid was decanted. The packets were washed with DMF (40 mlx2), DCM (40 mlx3) and shaken with a solution of 2-nitrobenzaldehyde in DCM (1.0M, 40 ml) in the presence of anhydrous sodium sulfate (20 g) at room temperature over the weekend (72 hrs). The packets were washed with DCM (40 mlx4) and dried under high vacuum over phosphorous pentoxide for 4 hrs.

2. [2+2] Cycloaddition

The dried packets were suspended in anhydrous DCM (80 ml) in a 250 ml round-bottomed flask under nitrogen atmosphere and cooled to −78° C. TEA (8.4 ml, 60 mmol) and a solution of 4-chlorophenoxyacetyl chloride (6.2 ml, 40 mmol) in anhydrous DCM (20 ml) were added sequentially via syringes. The mixture was stirred overnight (12 hrs) and allowed to warm to room temperature. The packets were washed with DCM (100 ml×2), methanol (100 ml×1), DMF (100 ml×2), DCM (100 ml×2) and air-dried.

To examine the [2+2] cycloaddition one packet from each resin was treated separately with 95% TFA in water (5 ml) at room temperature for 1 hr. The TFA solutions were collected in scintillation vials and the packets were extracted with acetic acid (HOAc) (5 ml×2). The TFA was removed by lyophilization. The individual residue was dissolved in the corresponding combined HOAc extracts and lyophilized to give the β-lactam intermediates.

From the above reactions with alanine, 1-(1-carboxyl) ethyl-3-(4-chlorophenoxy)-4-(2-nitrophenyl)azetidin-2-one (a mixture of two diastereoisomers, 2:3 by $^1$H NMR) resulted: yellowish powder (34.5 mg, >100%). $^1$H NMR (DMSO-$d_6$) δ 1.23(d, 3H), 1.64(d, 3H), 4.07(q, 1H), 4.43(q, 1H), 5.66(d, 1H), 5.77(d, 1H), 5.81(d, 1H), 5.86(d, 1H), 6.81(d, 3H), 6.89(d, 2H), 7.18(d, 3H), 7.29(d, 2H), 7.59(m, 2H), 7.81(m, 3H), 7.92(m, 1H), 8.07(m, 2H).

From the above reactions using glycine,-1-(carboxyl) methyl-3-(4-chlorophenoxy)-4-(2-nitrophenyl)azetidin-2-one resulted: yellowish powder (36.0 mg, >100%), $^1$H NMR (CDCl$_3$) δ 4.68(m, 3H), 5.78(m, 1H), 7.00(m, 4H), 7.70(m, 5H).

The reactions with phenylalanine yielded 1-(1-carboxyl-2-phenyl)ethyl-3-(4-chlorophenoxy)-4-(2-nitrophenyl) azetidin-2-one (a mixture of two diastereoisomers, 1:1 by $^1$H NMR): white powder (40.3 mg, >100%). $^1$H NMR (CDCl$_3$) δ 3.29(m, 1H), 3.46(m, 1H), 3.88(m, 2H), 4.31(m, 1H), 4.79(d, 1H), 5.30(d, 1H), 5.51(d, 1H), 5.52(d, 1H), 6.29(d, 1H), 6.70(m, 4H), 7.08(m, 8H), 7.27(m, 6H), 7.40(m, 4H), 7.65(m, 4H), 7.99(m, 2H).

3. Reduction-Rearrangement

The remaining three packets (one from each resin) were placed in a 60 ml polypropylene bottle and shaken with a solution of SnCl$_2$.2H$_2$O in DMF (2.0M, 40 mL) at room temperature for 15 hrs. The packets were washed with DMF (40 ml×5), methanol (40 ml×2), DCM (40 ml×2), air-dried and refluxed in dioxane (80 ml) for 20 hrs. The packets were washed with DCM (40 ml×2), air-dried and treated with 95% TFA in water (5 ml) separately at room temperature for 1 hr. The TFA solutions were collected in scintillation vials and the packets were extracted with HOAc (5 ml×2). The TFA was removed by lyophilization. The residues were dissolved in the corresponding combined HOAc extracts and lyophilized to give 4-(N-substituted)amino-3,4-dihydro-3-(4-chlorophenoxy)-2(1H)-quinolinones

EXAMPLE 2

4-[N-(1-Carboxylethyl)amino]-3,4-dihydro-3-(4-chlorophenoxy)-2(1H)-quinolinone

From alanine resulted a mixture of two diastereoisomers (1:1 by $^1$H NMR): yellowish powder (28.5 mg, >100%), $^1$H NMR (DMSO-$d_6$) δ 1.15(d, 3H), 1.25(d, 3H), 3.21(q, 1H), 3.71(q, 1H), 4.19(m, 2H), 4.93(bd, 2H), 6.95(m, 4H), 7.05 (m, 4H), 7.18(m, 2H), 7.30(m, 8H), 7.41(m, 2H),10.46(bs, 1H), 10.51(bs, 1H).

EXAMPLE 3

4-[(N-Carboxylmethyl)amino]-3,4-dihydro-3-(4-chlorophenoxy)-2(1H)-quinolinone

From glycine resulted a mixture of two diastereoisomers in a yield of 1.9 mg.

EXAMPLE 4

4-[N-(1-Carboxyl-2-phenylethyl)amino]-3,4-dihydro-3-(4-chlorophenoxy)-2(1H)-quinolinone From phenylalanine starting material, a mixture of two diastereoisomers (1:1 by $^1$H NMR) resulted: white powder (23.7 mg, 61%). $^1$H NMR (DMSO-$d_6$) δ 2.78(m, 2H), 2.93(m, 1H), 3.40(m, 2H), 3.80(m, 1H), 4.06(m, 2H), 4.87 (d, 1H), 4.94(d, 1H), 7.15(m, 30H), 10.41(bs, 1H), 10.45(bs, 1H)

EXAMPLE 5 TO EXAMPLE 19

Using the same experimental procedures of Examples 2 through 4, additional quinolinones (Example 5 to Example 19) were synthesized. Examples 5 to 19 provide all possible combinations of three amino acids and five different 2-nitrobenzaldehydes combined with, as the acid chloride component, benzyloxyacetyl chloride (BnOCH$_2$COCl, wherein "Bn" stands for benzyl). The amino acids and 2-nitrobenzaldehydes used, along with the corresponding Example number, are shown in Table I.

TABLE I

|  | Gly | L-Ala | L-Phe |
|---|---|---|---|
| 2-Nitro-benzaldehyde | Example 5 | Example 10 | Example 15 |
| 2-Chloro-6-nitro-benzaldehyde | Example 6 | Example 11 | Example 16 |
| 6-Nitro-veratraldehyde | Example 7 | Example 12 | Example 17 |
| 2,4-Dinitro-benzaldehyde | Example 8 | Example 13 | Example 18 |
| 5-Hydroxy 2-nitro-benzaldehyde | Example 9 | Example 14 | Example 19 |

EXAMPLE 5

4-[N-(Carboxylmethyl)amino]-3,4-dihydro-3-benzyloxy-2(1H)-quinolinone

Yield: 3.4 mg.

EXAMPLE 6

4-[N-(Carboxylmethyl)amino]-3,4-dihydro-3-benzyloxy-5-chloro-2(1H)-quinolinone

Yield: 3.1 mg.

EXAMPLE 7

4-[N-(Carboxylmethyl)amino]-3,4-dihydro-3-benzyloxy-6,7-dimethoxy-2(1H)-quinolinone Yield: 16.1 mg, 51%. $^1$H NMR (DMSO-$d_6$) δ 3.63(s, 3H), 3.70(s, 3H), 4.39(d, 1H), 4.53(s, 2H), 4.57(d, 1H), 5.01(d, 1H), 5.19(d, 1H), 6.57(s, 1H), 7.19(s, 1H), 7.31(m, 5H), 8.25(m, 2H), 10.21(bs, 1H).

EXAMPLE 8

4-[N-(Carboxylmethyl)amino]-3,4-dihydro-3-benzyloxy-7-amino-2(1H)-quinolinone

Yield: 1.8 mg.

EXAMPLE 9

4-[N-(Carboxylmethyl)amino]-3,4-dihydro-3-benzyloxy-6-hydroxy-2(1H)-quinolinone

Yield: 5.6 mg.

EXAMPLE 10

4-[N-(1-Carboxylethyl)amino]-3,4-dihydro-3-benzyloxy-2(1H)-quinolinone

Yield: 16.6 mg, 68%. A mixture of two diastereomer (1:1): $^1$H NMR (DMSO-d$_6$) δ 1.04(d, 3H), 1.12(d, 3H), 2.98(q, 1H), 3.34(q, 1H), 3.79(m, 1H), 3.92(m, 3H), 4,58(m, 4H) 6.90(m, 4H), 7.28(m, 18H), 10.21(bs, 1H), 10.25(bs, 1H). MS: found 341(M+1), 363(M+Na).

EXAMPLE 11

4-[N-(1-Carboxylethyl)amino]-3,4-dihydro-3-benzyloxy-5-chloro-2(1H)-quinolinone

Yield: 24.4 mg.

EXAMPLE 12

4-[N-(1-Carboxylethyl)amino]-3,4-dihydro-3-benzyloxy-6,7-dimethoxy-2(1H)-quinolinone Yield: 24.3 mg, 84%.

EXAMPLE 13

4-[N-(1-Carboxylethyl)amino]-3,4-dihydro-3-benzyloxy-7-amino-2(1H)-quinolinone

Yield: 3.6 mg.

EXAMPLE 14

4-[N-(1-Carboxylethyl)amino]-3,4-dihydro-3-benzyloxy-6-hydroxy-2(1H)-quinolinone Yield: 10.4 mg, 41%.

EXAMPLE 15

4-[N-(1-Carboxyl-2-phenylethyl)amino]-3,4-dihydro-3-benzyloxy-2(1H)-quinolinone

Yield: 21.2 mg, 65%.

EXAMPLE 16

4-[N-(1-Carboxyl-2-phenylethyl)amino]-3,4-dihydro-3-benzyloxy-5-chloro-2(1H)-quinolinone Yield: 9.9 mg.

EXAMPLE 17

4-[N-(1-Carboxyl-2-phenylethyl)amino]-3,4-dihydro-3-benzyloxy-6,7-dimethoxy-2(1H)-quinolinone Yield: 30.3 mg, 82%.

EXAMPLE 18

4-[N-(1-Carboxyl-2-phenylethyl)amino]-3,4-dihydro-3-benzyloxy-7-amino-2(1H)-quinolinone Yield: 3.2 mg.

EXAMPLE 19

4-[N-(1-Carboxyl-2-phenylethyl)amino]-3,4-dihydro-3-benzyloxy-6-hydroxy-2(1H)-quinolinone Yield: 23.5 mg, 70%.

EXAMPLE 20 TO EXAMPLE 34

Using the same experimental procedures of Examples 2 through 4, additional quinolinones (Example 20 to Example 34) were synthesized. Having an acid chloride component of acetoxyacetyl chloride (CH$_3$C(O)OCH$_2$COCl), Example 20 to 34 provide all possible combinations of three amino acids and five unique 2-nitrobenzaldehydes. The amino acids and 2-nitrobenzaldehydes used, along with the corresponding Example number are shown in Table II.

TABLE II

|  | Gly | L-Ala | L-Phe |
|---|---|---|---|
| 2-Nitrobenzaldehyde | Example 20 | Example 25 | Example 30 |
| 2-Chloro-6-nitro-benzaldehyde | Example 21 | Example 26 | Example 31 |
| 6-Nitro-veratraldehyde | Example 22 | Example 27 | Example 32 |
| 2,4-Dinitrobenzaldehyde | Example 23 | Example 28 | Example 33 |
| 5-Hydroxy-2-nitro-benzaldehyde | Example 24 | Example 29 | Example 34 |

EXAMPLE 20

4-[N-(Carboxylmethyl)amino]-3,4-dihydro-3-acetoxy-2(1H)-quinolinone

Yield: 5.6 mg.

EXAMPLE 21

4-[N-(Carboxylmethyl)amino]-3,4-dihydro-3-acetoxy-5-chloro-2(1H)-quinolinone

Yield: 4.2 mg.

EXAMPLE 22

4-[N-(Carboxylmethyl)amino]-3,4-dihydro-3-acetoxy-6,7-dimethoxy-2(1H)-quinolinone Yield: 15.5 mg, 55%.

EXAMPLE 23

4-[N-(Carboxylmethyl)amino]-3,4-dihydro-3-acetoxy-7-amino-2(1H)-quinolinone

Yield: 5.3 mg.

EXAMPLE 24

4-[N-(Carboxylmethyl)amino]-3,4-dihydro-3-acetoxy-6-hydroxy-2(1H)-quinolinone

Yield: 8.4 mg.

EXAMPLE 25

4-[N-(1-Carboxylethyl)amino]-3,4-dihydro-3-acetoxy-2(1H)-quinolinone

Yield: 18.9 mg, 90%. MS: found 293(M+1), 315(M+Na), 582 (2M+1).

EXAMPLE 26

4-[N-(1-Carboxylethyl)amino]-3,4-dihydro-3-acetoxy-5-chloro-2(1H)-quinolinone

Yield: 4.3 mg.

EXAMPLE 27

4-[N-(1-Carboxylethyl)amino]-3,4-dihydro-3-acetoxy-6,7-dimethoxy-2(1H)-quinolinone Yield: 23.3 mg, 92%.

EXAMPLE 28

4-[N-(1-Carboxylethyl)amino]-3,4-dihydro-3-acetoxy-7-amino-2(1H)-quinolinone

Yield: 5.2 mg.

EXAMPLE 29

4-[N-(1-Carboxylethyl)amino]-3,4-dihydro-3-acetoxy-6-hydroxy-2(1H)-quinolinone

Yield: 14.4 mg, 65%.

EXAMPLE 30

4-[N-(1-Carboxyl-2-phenylethyl)amino]-3,4-dihydro-3-acetoxy-2 (1H)-quinolinone

Yield: 26.0 mg, 91%.

EXAMPLE 31

4-[N-(1-Carboxyl-2-phenylethyl)amino]-3,4-dihydro-3-acetoxy-5-chloro-2(1H)-quinolinone Yield: 6.2 mg.

EXAMPLE 32

4-[N-(1-Carboxyl-2-phenylethyl)amino]-3,4-dihydro-3-acetoxy-6,7-dimethoxy-2(1H)-quinolinone Yield: 29.9 mg, 90%.

EXAMPLE 33

4-[N-(1-Carboxyl-2-phenylethyl)amino]-3,4-dihydro-3-acetoxy-7-amino-2(1H)-quinolinone Yield: 4.6 mg.

EXAMPLE 34

4-[N-(1-Carboxyl-2-phenylethyl)amino]-3,4-dihydro-3-acetoxy-6-hydroxy-2(1H)-quinolinone Yield: 25.7 mg, 86%.

EXAMPLE 35 TO EXAMPLE 37

4-[(N-Substituted)amino]-3,4-dihydro-3-phenoxy-2 (1H)-quinolinones

These examples provide the solid-phase synthesis of diastereoisomeric mixtures (approximately 1:1) of 4-(N-substituted)amino-3,4-dihydro-3-phenoxy-2(1H)-quinolinone by condensing 2-nitrobenzaldehyde, phenoxyacetyl chloride and amino acids on a polystyrene MBHA resin. The quinolinones were cleaved from the solid support by HF cleavage.

Boc-L-Ala-MBHA-resin (Advanced ChemTech, lot # 13381, 0.55 mmol/g), Boc-Gly-MBHA-resin (Advanced ChemTech, lot # 12588, 0.75 mmol/g) and Boc-L-Phe-MBHA-resin (Advanced ChemTech, lot # 14316, 0.75 mmol/g) were placed separately in three porous polypropylene packets (1 packet/resin, 100 mg/packet). The packets were placed in a 60 ml polypropylene bottle and shaken with a solution of 55% TFA in DCM (30 ml) at room temperature for 35 mins. The liquid was decanted, the packets washed with DCM (30 ml×3), 5% DIEA in DCM (30 ml×3) and DCM (30 ml×3), and shaken with a solution of 2-nitrobenzaldehyde in DCM (1.0M, 40 ml) in the presence of anhydrous sodium sulfate (20 g) at room temperature over the weekend (60 hrs). The packets were washed with DCM (40 ml×4) and dried under high vacuum over phosphorous pentoxide for 4 hrs.

The dried packets were suspended in anhydrous DCM (80 ml) in a 150 ml polypropylene bottle under nitrogen atmosphere and cooled to −78° C. TEA (17 ml, 120 mmol) and a solution of phenoxyacetyl chloride (11 ml, 80 mmol) in anhydrous DCM (20 ml) were added sequentially by syringe. The mixture was allowed to stand in a dry ice box overnight (12 hrs) and allowed to warm to room temperature. The packets were washed with DCM (100 ml×2), methanol (100 ml×1), DMF (100 ml×2), DCM (100 ml×2) and air-dried.

The packets were then placed in a 60 ml polypropylene bottle and shaken with a solution of $SnCl_2.2H_2O$ in DMF (2.0M, 40 ml) at room temperature for 15 hrs. The packets were washed with DMF (40 ml×5), methanol (40 ml×2), DCM (40 ml×2) and air-dried. The packets were treated separately on a HF cleavage apparatus with a mixture of HF and anisole (5 ml, 95:5) at −5° C. for 1.5 hrs. The HF was removed with a nitrogen stream. The residues were extracted with HOAc (5 ml×3). The combined HOAc extracts were lyophilized to give the quinolinones.

EXAMPLE 35

4-[N-(2-Propionamidoyl)amino]-3,4-dihydro-3-phenoxy-2(1H)-quinolinone

From the alanine starting material, resulted a mixture of two diastereoisomers (1:1 by $^1$H NMR): white powder (17.8 mg, 100 ), $^1$H NMR (DMSO-$d_6$) δ 1.12(d, 3H), 1.18(d, 3H), 3.00(q, 1H), 3.39(q, 1H), 3.90(d, 1H), 3.96(d, 1H), 4.76(d, 1H), 4.81(d, 1H), 6.95(m, 12H), 7.25(m, 10H), 10.39(bs, 2H); MS: found 326(M+1), 348(M+Na).

EXAMPLE 36

4-[N-(2-Acetamidoyl)amino]-3,4-dihydro-3-phenoxy-2(1H)-quinolinone

The glycine starting material resulted in a white powder (22.3 mg, >100%): $^1$H NMR (DMSO-$d_6$) δ 3.20(bs, 2H), 4.09(d, 1H), 4.90(d, 1H), 6.96(m, 6H), 7.26(m, 5H), 10.38 (bs, 1H). MS: found 312(M+1), 623(2M+1).

EXAMPLE 37

4-[N-(3-Phenyl-2-propionamidoyl)amino]-3,4-dihydro-3-phenoxy-2(1H)-quinolinone

The phenyalanine starting material yielded a mixture of two diastereoisomers (1:1 by $^1$H NMR): white powder (25.8 mg, 86%). $^1$H NMR (DMSO-$d_6$) δ 2.79(m, 3H), 3.35(t, 1H), 3.65(m, 2H), 3.80(m, 2H), 4.70(d, 1H), 4.76(d, 1H), 6.90(m, 11H), 7.15(m, 19H), 7.40(m, 3H), 10.38(bs, 2H). MS: found 402 (M+1), 424(M+Na).

EXAMPLE 38

4-[N-(4-Carboxamidoylphenyl)amino]-3,4-dihydro-3-phenoxy-2(1H)-quinolinone

This example provides the solid-phase synthesis of 4-[N-(4-carboxamidoylphenyl)amino]-3,4-dihydro-3-phenoxy-2

(1H)-quinolinone by condensing 2-nitrobenzaldehyde, phenoxyacetyl chloride and 4-aminobenzoic acid on a polystyrene MBHA resin. The quinolinone was cleaved from the solid support by HF cleavage.

Polystyrene MBHA resin (0.90 mmol/g) was placed in two porous polypropylene packets (100 mg/packet). The packets were washed with 5% DIEA in DCM (30 ml×3) and DCM (30 ml×3). The packets were shaken with 4-aminobenzoic acid (1.03 g, 7.5 mmol), HOBT (1.01 g, 7.5 mmol) and DIC (1.41 ml, 9.0 mmol) in DMF (30 ml) at room temperature overnight (21 hrs). The packets were washed with DMF (30 ml×3), DCM (30 ml×3) and air-dried.

The packets were shaken with a solution of 2-nitrobenzaldehyde in DCM (1.0M, 40 ml) in the presence of anhydrous sodium sulfate (20 g) at room temperature over the weekend. The packets were washed with DCM (40 ml×4) and dried under high vacuum over phosphorous pentoxide overnight.

The dried packets were suspended in anhydrous DCM (30 ml) in a 60 ml polypropylene bottle under nitrogen atmosphere and cooled to −78° C. TEA (4.2 ml, 30 mmol) and a solution of phenoxyacetyl chloride (2.8 ml, 20 mmol) in anhydrous DCM (10 ml) were added sequentially via syringes. The mixture was allowed to stand in a dry ice box overnight (12 hrs) and allowed to warm to room temperature over a 5-hour period. The packets were washed with DCM (40 ml×2), methanol (40 ml×1), DMF (40 ml×2), DCM (40 ml×2) and air-dried.

To monitor the [2+2] cycloaddition reaction, one packet was treated with HF and anisole (95:5) at −5° C. for 1.5 hrs. The HF was removed with a nitrogen stream. The residues were extracted with HOAc (5 ml×3). The combined HOAc extracts were lyophilized to give the 1-(4-carboxamidoylphenyl)-3-phenoxy-4-(2-nitrophenyl) azetidin-2-one as yellowish powder (36.1 mg, 100%): $^1$H NMR (DMSO-$d_6$) δ 6.10 (d, 1H), 6.30 (d, 1H), 6.90(m, 4H), 7.32(m, 5H), 7.68(m, 2H), 7.90(m, 3H), 8.25(m, 1H).

The remaining packet was placed in a 30 ml polypropylene bottle and shaken with a solution of $SnCl_2.2H_2O$ in DMF (2.0M, 20 ml) at room temperature for 15 hrs. The packet was washed with DMF (20 ml×5), methanol (20 ml×2), DCM (20 ml×2), air-dried. The packet was treated on a HF cleavage apparatus with a mixture of HF and anisole (5 ml, 95:5) at −5° C. for 1.5 hrs. The HF was removed with a nitrogen stream. The residue was extracted with HOAc (5 ml×3). The combined HOAc extracts was lyophilized to give the quinolinone as white powder (37.9 mg, 100%): $^1$H NMR (DMSO-$d_6$) δ 4.98(d, 1H), 5.25(m, 1H), 6.70(m, 2H), 6.90(m, 6H), 7.20(m, 5H), 7.65(m, 4H), 10.55(bs, 1H).

EXAMPLE 39

4-[N-(4-Carboxamidoylbenzyl)amino]-3,4-dihydro-3-phenoxy-2(1H)-quinolinone

This example provides the solid-phase synthesis of 4-[N-(4-carboxamidoylbenzyl)amino]-3,4-dihydro-3-phenoxy-2 (1H)-quinolinone by condensing 2-nitrobenzaldehyde, phenoxyacetyl chloride and 4-(N-Boc-aminomethyl)benzoic acid on a polystyrene MBHA resin. The quinolinone was cleaved from the solid support by HF cleavage.

Polystyrene MBHA resin (0.90 mmol/g) was placed in two porous polypropylene packets (100 mg/packet). The packets were washed with 5% DIEA in DCM (30 ml×3) and DCM (30 ml×3). The packets were shaken with 4-(N-Boc-aminomethyl)benzoic acid (1.88 g, 7.5 mmol), HOBT (1.01 g, 7.5 mmol) and DIC (1.41 ml, 9.0 mmol) in DMF (30 ml) at room temperature overnight (21 hrs). The packets were washed with DMF (30 ml×3), DCM (30 ml×3) and air-dried.

The packets were placed in a 20 ml polypropylene bottle and shaken with a solution of 55% TFA in DCM (15 ml) at room temperature for 30 mins. The liquid was decanted. The packets were washed with DCM (20 ml×3), 5% DIEA in DCM (20 ml×3), DCM (20 ml×3) and shaken with a solution of 2-nitrobenzaldehyde in DCM (1.0M, 15 ml) in the presence of anhydrous sodium sulfate (10 g) at room temperature over the weekend (60 hrs). The packets were washed with DCM (20 ml×4) and dried under high vacuum over phosphorous pentoxide overnight.

The dried packets were suspended in anhydrous DCM (30 ml) in a 60 ml polypropylene bottle under nitrogen atmosphere and cooled to −78° C. TEA (4.2 ml, 30 mmol) and a solution of phenoxyacetyl chloride (2.8 ml, 20 mmol) in anhydrous DCM (10 ml) were added sequentially via syringes. The mixture was allowed to stand in a dry ice box overnight (12 hrs) and allowed to warm to room temperature over a 5-hr period. The packets were washed with DCM (40 ml×2), methanol (40 ml×1), DMF (40 ml×2), DCM (40 ml×2) and air-dried.

To monitor the [2+2] cycloaddition reaction, one packet was treated with HF and anisole (95:5) at −5° C. for 1.5 hrs. The HF was removed with a nitrogen stream. The residues were extracted with HOAc (5 ml×3). The combined HOAc extracts were lyophilized to give the 1-(4-carboxamidoylbenzyl)-3-phenoxy-4-(2-nitrophenyl) azetidin-2-one as yellowish powder (36.1 mg, 100%): $^1$H NMR (DMSO-$d_6$) δ 4.40(bd, 1H), 4.85(bd, 1H), 5.55(bs, 1H), 5.95(bs, 1H), 6.80(m, 4H), 7.30(m, 5H), 7.75(m, 8H).

The other packet was placed in a 30 ml polypropylene bottle and shaken with a solution of $SnCl_2.2H_2O$ in DMF (2.0M, 20 ml) at room temperature for 15 hrs. The packet was washed with DMF (20 ml×5), methanol (20 ml×2), DCM (20 ml×2), air-dried. The packet was treated on a HF cleavage apparatus with a mixture of HF and anisole (5 ml, 95:5) at −5° C. for 1.5 hrs. The HF was removed with a nitrogen stream. The residue was extracted with HOAc (5 ml×3). The combined HOAc extract was lyophilized to give the quinolinone as white powder (37.9 mg, 100%): $^1$H NMR (DMSO-$d_6$) δ 3.80(bs, 2H), 4.10(bs, 1H), 4.95(bs, 1H), 6.95(m, 6H), 7.30(m, 8H), 7.85(m, 4H), 10.45(bs, 1H).

EXAMPLE 40

Solid-phase synthesis of a library of 4,260 different 4-amino-quinolinones (2130 pairs of enantiomers)

Seventy-two porous polypropylene packets containing polystyrene MBHA resin (0.90 mmol/g, 150 mg/packet) were prepared. Thirty additional porous polypropylene packets ("sister-packets") containing the same polystyrene MBHA resin (100 mg/packet) were also prepared. One packet and five sister-packets were placed in a 40 ml polypropylene bottle followed by addition of Nα-Boc-L-Ala (605.6 mg, 32.0 mmol), a freshly prepared solution of HOBT in DMF (0.20M, 16.0 ml), a freshly prepared solution of DIC in DMF (0.20M, 16.0 ml) and DIEA (1.18 ml, 12.3 mmol). The mixture was shaken at room temperature for 20 hrs. The liquid was decanted and the packets washed with DMF (30 ml×3), MeOH (30 ml×2) and DCM (30 ml×3), and then air-dried. The same procedure was carried out with other five packets, each accompanied with five sister-packets and each being coupled separately with one of the five following amino acids: 4-aminobenzoic acid, 4-(N-Boc-aminomethyl)benzoic acid, Nα-Boc-β-benzyl-aspartate, Nα-Boc-L-Phg and Nα-Boc-L-Val. The remaining sixty-five packets were each placed in an individual 10 mL polypropylene bottle. To each bottle were added a freshly prepared solution of HOBT in DMF (0.20M, 4.0 ml), a freshly prepared solution of DIC in DMF (0.20M, 4.0 ml), DIEA (236 ml, 2.5 mmol) and an amino acid from the following list: Boc-β-Ala, Boc-γ-Abu, Boc-6-amino-caproic acid, Boc-ε-amino-hexanoic acid, Boc-7-amino-heptanoic acid, Boc-α-Aib, 3-aminobenzoic acid, 4-amino-2-chlorobenzoic acid, Boc-D-Nva, Boc-D-Ala, Boc-D-Nle, Boc-D-3-(2-Naph)-Ala, Boc-D-β-thienyl-Ala, Boc-D-Phe(-p-NO$_2$), Boc-D-p-chloro-Phe, Boc-D-Tyr(OEt), Boc-D-p-fluoro-Phe, Boc-D-Tyr(O-2,6-Cl$_2$-Bzl), Boc-D-Trp(CHO), Boc-D-Asn, Boc-D-β-cycloHex-Ala, Boc-D-Ser(Bzl), Boc-D-Thr(Bzl), Boc-D-Cys(-S-p-OCH$_3$-Bzl), Boc-D-Ile, Boc-D-Val, Boc-D-Phe, Boc-D-Gln, Boc-D-Glu-γ-Bzl, Boc-D-Leu.H$_2$O, Boc-D-citrulline, α-Boc-ε-Fmoc-D-Lys, Boc-D-Lys(ε-2-Cl-Cbz), Boc-D-Met, Boc-D-Phg, Boc-L-Nva, Boc-L-Nle, Boc-L-α-Abu, ε-Boc-α-Z-L-Lys, Boc-L-3-(2-Naph)-Ala, Boc-L-β-thienyl-Ala, Boc-L-3-(3-Pyridyl)-Ala, Boc-L-Phe(-p-NO$_2$), Boc-L-p-chloro-Phe, Boc-L-Tyr(OEt), Boc-L-p-fluoro-Phe, Boc-L-Tyr(O-2,6-Cl$_2$-Bzl), Boc-L-Asn, Boc-L-isoasparagine, Boc-L-Asp-α-Bzl, Boc-L-β-cycloHex-Ala, Boc-L-Ser(Bzl), Boc-L-Thr(Bzl), Boc-L-Cys(-S-p-OCH$_3$-Bzl), Boc-L-Ile.1/2 H$_2$O, Boc-L-Phe, Boc-L-Gln, Boc-L-isoglutamine, Boc-L-Glu-α-Bzl, Boc-L-Leu.H$_2$O, Boc-L-Lys(Ac), Boc-L-Lys(ε-2-Cl-Cbz), Di-Boc-L-Lys, Boc-L-methionine sulfoxide, Boc-L-α-t-BuGly, and Boc-Gly.

The bottles were shaken at room temperature for 20 hrs and the liquid decanted from each bottle. The packets were pooled into a 1 L polypropylene bottle and washed with DMF (700 ml×3), MeOH (700 ml×2), DCM (700 ml×3) and air-dried. A small amount of resin was sampled from each packet, not including the sister-packets. Ninhydrin test was carried out separately with each resin sample. The coupling step was repeated with ones having a positive ninhydrin test result. After achieving complete coupling for every amino acid, all packets (except the sister-packets) were opened. All resins were pooled into a large porous polypropylene packets (15 cm×20 cm) and mixed by shaking with DCM (1 L) in a 2 L polypropylene bottle for 4 hrs. The packet was air-dried followed by drying under high vacuum over phosphorus pentoxide overnight. The resulting resin (12.782 g) was distributed into ninety porous polypropylene packets (140 mg/packet). The ninety packets along with the thirty sister-packets were placed in a 1 L polypropylene bottle and shaken with 55% TFA (700 ml) in DCM for 30 mins. The liquid was decanted. The packets were washed with DCM (700 ml×2), 5% DIEA in DCM (700 ml×2), MeOH (700 ml×2) and DCM (700 ml×3), and then air-dried.

Using the same experimental procedures of Examples 35 through 37, thirty pools (Pool 1 to 30) of quinolinones (142 quinolinones per pool) in triplicates (three packets per pool) were synthesized simultaneously. Pool 1 through 30 provide all possible combinations of five acid chlorides and six 2-nitrobenzaldehydes. The acid chlorides and 2-nitrobenzaldehydes used, along with the corresponding Pool number are shown in Table 3. One sister-packet along with each pool was also carried along each pool to evaluate the efficiency of the reaction process. One copy of the library (30 packets, one packet from each pool) was pooled in a polypropylene bottle and shaken with a mixture of HF, p-cresol, ethanedithiol and dimethylsulfide (120 ml; 25:10:5:60) at 0° C. for 2 hrs to remove the protecting groups. The packets were washed with DCM, isopropanol and DMF alternatively until no thiol odor remained (about 25 washes). The packets were treated with HF under standard cleavage conditions to give a library of 4260 different quinolinones. The other two copies of the library were kept on the resin for later use.

TABLE III

| | Methoxy-acetyl-chloride | Phenoxy-acetyl-chloride | Benzyloxy-acetyl-chloride | Acetoxy-acetyl-chloride | 4-Chloro-phenoxy-acetyl-chloride |
|---|---|---|---|---|---|
| 2-Nitro-benzaldehyde | Pool 1 | Pool 2 | Pool 3 | Pool 4 | Pool 5 |
| 6-Nitro-piperonal | Pool 6 | Pool 7 | Pool 8 | Pool 9 | Pool 10 |
| 6-Nitro-veratraldehyde | Pool 11 | Pool 12 | Pool 13 | Pool 14 | Pool 15 |
| 5-Chloro-2-nitro-benzaldehyde | Pool 16 | Pool 17 | Pool 18 | Pool 19 | Pool 20 |
| 3-Methoxy-2-nitro-benzaldehyde | Pool 21 | Pool 22 | Pool 23 | Pool 24 | Pool 25 |
| 5-Hydroxy-2-ntiro-benzaldehyde | Pool 26 | Pool 27 | Pool 28 | Pool 29 | Pool 30 |

EXAMPLE 41

Identification of Kappa Opioid Selective Compounds By A Radioreceptor Assay

This example describes the identification of compounds contained within a synthetic combinatorial library mixture which bind to the κ opioid receptor and are inhibitors thereof.

The assay was carried out as described above in the Detailed Description. The composition of the tetrohydroquinoline mixtures tested is identified in Table III in the prior Example. As shown in the following Table IV, many of the subject compounds are selective for the κ opioid receptor.

TABLE IV

| BINDING TO KAPPA OPIOID RECEPTOR | |
|---|---|
| Mixture | Percent Bound |
| 2 | 53.96 |
| 15 | 55.07 |
| 22 | 56.12 |
| 5 | 67.83 |
| 14 | 69.99 |
| 30 | 70.45 |
| 13 | 71.50 |
| 16 | 72.96 |
| 23 | 73.43 |
| 4 | 75.58 |
| 29 | 79.26 |
| 24 | 80.59 |
| 21 | 82.63 |
| 25 | 83.10 |
| 1 | 86.77 |
| 28 | 87.82 |
| 26 | 90.38 |
| 3 | 97.67 |
| 27 | 99/01 |
| 8 | 105.19 |
| 20 | 107.34 |
| 7 | 114.86 |
| 19 | 119.29 |
| 17 | 120.57 |
| 11 | 120.86 |
| 6 | 121.68 |
| 12 | 130.36 |
| 18 | 143.47 |

TABLE IV-continued

BINDING TO KAPPA OPIOID RECEPTOR

| Mixture | Percent Bound |
|---|---|
| 9 | 168.59 |
| 10 | 180.89 |

EXAMPLE 42

Identification of Mu Opioid Selective Compounds By A Radioreceptor Assay

This example describes the identification of compounds contained within a synthetic combinatorial library mixture which bind to the μ opioid receptor and are inhibitors thereof.

The assay was carried out as described above in the Detailed Description. The composition of the tetrohydro-quinoline mixtures tested is identified in Table III in Example 40. As shown in the following Table V, many of the subject compounds contained with the mixtures are selective for the μ opioid receptor.

TABLE V

BINDING TO MU OPIOID RECEPTOR

| Mixture | Percent Bound |
|---|---|
| 4 | 29.61 |
| 2 | 26.98 |
| 1 | 38.94 |
| 22 | 39.43 |
| 5 | 43.12 |
| 25 | 43.98 |
| 17 | 49.51 |
| 27 | 51.97 |
| 29 | 53.44 |
| 12 | 53.81 |
| 16 | 55.28 |
| 6 | 55.90 |
| 3 | 56.02 |
| 26 | 57.37 |
| 28 | 57.49 |
| 24 | 58.97 |
| 14 | 59.10 |
| 21 | 59.83 |
| 13 | 60.81 |
| 30 | 63.14 |
| 20 | 63.14 |
| 15 | 64.00 |
| 8 | 66.58 |
| 23 | 66.83 |
| 7 | 68.43 |
| 10 | 68.55 |
| 11 | 69.53 |
| 9 | 70.64 |
| 19 | 76.90 |
| 18 | 77.89 |

Although the invention has been described with reference to the examples provided above, it should be understood that various modifications can be made by those skilled in the art without departing from the invention. Accordingly, the invention is set out in the following claims.

We claim:
1. A library of two or more tetrahydro-quinoline compounds of the formula:

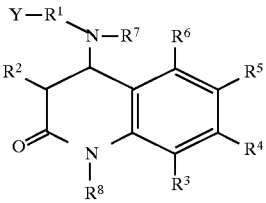

FORMULA I wherein:
$R^1$ is selected from the group consisting of $C_1$ to $C_6$ alkyl, $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl or a group of the formula:

wherein n and m are independently selected from a number 0 to 6; and Ar is an aryl group selected from the group consisting of phenyl, substituted phenyl, heteroaryl and substituted heteroaryl;

$R^1$ is selected from the group consisting of hydroxy, $C_1$ to $C_7$ alkoxy, $C_1$ to $C_7$ substituted alkoxy, $C_1$ to $C_7$ acyloxy, $C_7$ to $C_{12}$ phenylalkoxy, $C_7$ to $C_{12}$ substituted phenylalkoxy, phenoxy, substituted phenoxy, phthalimide, substituted phthalimide, amino, protected amino (monosubstituted)amino, (disubstituted)amino, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^3$, $R^4$, $R^5$ and $R^6$ are, independently, selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ alkoxy, $C_1$ to $C_7$ substituted alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to $C_4$ alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^7$ and $R^8$ are, independently, selected from the group consisting of a hydrogen atom, $C_1$ to $C_6$ alkyl, $C_1$ to $C_6$ substituted alkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is $C(O)NHR^9$, wherein $R^9$ is a hydrogen atom, $C_1$ to $C_6$ alkyl and $C_1$ to $C_6$ substituted alkyl; or a salt of the tetrahydro-quinoline compounds.

2. The library of claim 6, wherein:

$R^1$ is selected from the group consisting of $C_1$ to $C_6$ alkyl, $C_1$ to $C_6$ substituted alkyl, $C_3$ to $C_7$ cycloalkyl, $C_3$ to $C_7$ substituted cycloalkyl, phenyl, substituted phenyl, $C_7$ to $C_{12}$ phenylalkyl, $C_7$ to $C_{12}$ substituted phenylalkyl or a group of the formula:

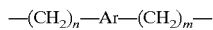

wherein n and m are independently selected from a number 0 to 3; and Ar is an aryl group selected from the group consisting of phenyl, substituted phenyl, heteroaryl and substituted heteroaryl;

$R^2$ is selected from the group consisting of hydroxy, $C_1$ to $C_7$ alkoxy, $C_1$ to $C_7$ substituted alkoxy $C_1$ to $C_7$ acyloxy, $C_7$ to $C_{12}$ phenylalkoxy, $C_7$ to $C_{12}$ substituted phenylalkoxy, phenoxy and substituted phenoxy;

$R^3$, $R^4$, $R^5$ and $R^6$ are, independently, selected from the group consisting of a hydrogen atom, halo, hydroxy, protected hydroxy, and $C_1$ to $C_7$ alkoxy;

$R^7$ and $R^8$ are each, independently, a hydrogen atom; and

Y is $C(O)NHR^9$, wherein $R^9$ is a hydrogen atom.

3. The library of claim 1, wherein:

$R^1$ is selected from the group consisting of 1,2-ethyl; 1,3-propyl; 1,4-butyl; 1,5-pentyl; 1,6-hexyl; 1-methyl-1,1-ethyl, 3-aminobenzoyl; 4-amino-2-chlorobenzoyl; 4-aminobenzoyl; 4-aminomethylbenzoyl; D-1,1-butyl; D-1,1-ethyl; D-1,1-pentyl; D-1,1-propyl; D-1-amino-1,5-pentyl; D-2-(2-naphthyl)-1,1-ethyl; D-2-(2-thienyl)-1,1-ethyl; D-2-(3-pyridyl)-1,1-ethyl; D-2-(4-aminophenyl)-1,1-ethyl; D-2-(4-chlorophenyl)-1,1-ethyl; D-2-(4-ethoxyphenyl)-1,1-ethyl; D-2-(4-fluorophenyl)-1,1-ethyl; D-2-(4-hydroxyphenyl)-1,1-ethyl; D-2-(N-formyl-indol-3-yl)-1,1-ethyl; D-2-carboxamido-1,1-ethyl; D-2-carboxamido-1,2-ethyl; D-2-carboxy-1,2-ethyl; D-2-cyclohexyl-1,1-ethyl; D-2-hydroxy-1,1-ethyl; D-2-hydroxy-1,1-propyl; D-2-mercapto-1,1-ethyl; D-2-methyl-1,1-butyl; D-2-methyl-1,1-propyl; D-2-phenyl-1,1-ethyl; D-3-carboxamido-1,1-propyl; D-3-carboxamido-1,3-propyl; D-3-carboxy-1,1-propyl; D-3-carboxy-1,3-propyl; D-3-methyl-1,1-butyl; D-4-ureido-1,1-butyl; D-5-(9-fluorenylmethoxycarboxamido)-1,1-pentyl; D-5-acetamido-1,1-pentyl; D-5-amino-1,1-pentyl; D-methylthio-1,1-propyl; D-phenylmethyl; D-t-butylmethyl; L-1,1-butyl; L-1,1-ethyl; L-1,1-pentyl; L-1,1-propyl; L-1-amino-1,5-pentyl; L-2-(2-naphthyl)-1,1-ethyl; L-2-(2-thienyl)-1,1-ethyl; L-2-(3-pyridyl)-1,1-ethyl; L-2-(4-aminophenyl)-1,1-ethyl; L-2-(4-chlorophenyl)-1,1-ethyl; L-2-(4-ethoxyphenyl)-1,1-ethyl; L-2-(4-fluorophenyl)-1,1-ethyl; L-2-(4-hydroxyphenyl)-1,1-ethyl; L-2-(N-formyl-indol-3-yl)-1,1-ethyl; L-2-carboxamido-1,1-ethyl; L-2-carboxamido-1,2-ethyl; L-2-carboxy-1,1-ethyl; L-2-carboxy-1,2-ethyl; L-2-cyclohexyl-1,1-ethyl; L-2-hydroxy-1,1-ethyl; L-2-hydroxy-1,1-propyl; L-2-mercapto-1,1-ethyl; L-2-methyl-1,1-butyl; L-2-methyl-1,1-propyl; L-2-phenyl-1,1-ethyl; L-3-carboxamido-1,1-propyl; L-3-carboxamido-1,3-propyl; L-3-carboxy-1,1-propyl; L-3-carboxy-1,3-propyl; L-3-methyl-1,1-butyl; L-4-ureido-1,1-butyl; L-5-acetamido-1,1-pentyl; L-5-amino-1,1-pentyl; 5-(4-amino-(3,4-dihydro-3-alkoxy)-2quinolinoyl)-1,1-pentyl; L-methylthio-1,1-propyl; L-phenylmethyl; L-t-butylmethyl; and methylene;

$R^2$ is selected from the group consisting of hydroxy; methoxy; phenoxy; benzyloxy; acetoxy; and 4-chlorophenoxy;

$R^3$ $R^4$, $R^5$, $R^6$ are, selected from the group consisting of when each are, independently, a hydrogen atom; $R^3$ and $R^6$ are each hydrogen when $R^4$ and $R^5$ are together methylenedioxy or $R^4$ and $R^5$ are each, independently, methoxy; $R^3$, $R^4$ and $R^6$ are each, independently, a hydrogen atom when $R^5$ is chloro or methoxy; and $R^3$ is methoxy when $R^4$, $R^5$ and $R^6$ are each, independently, a hydrogen atom;

$R^7$ and $R^8$ are each, independently, a hydrogen atom; and

Y is $C(O)NH_2$.

4. The library of claim 1, wherein:

$R^1$ is selected from the group consisting of 1,2-ethyl; 1,3-propyl; 1,4-butyl; 1,5-pentyl; 1,6-hexyl; 1-methyl-1,1-ethyl; 3-aminobenzoyl; 4-amino-2-chlorobenzoyl; 4-aminobenzoyl; 4-aminomethylbenzoyl; D-1,1-butyl; D-1,1-ethyl; D-1,1-pentyl; D-1,1-propyl; D-1-amino-1,5-pentyl; D-2-(2-naphthyl)-1,1-ethyl; D-2-(2-thienyl)-1,1-ethyl; D-2-(3-pyridyl)-1,1-ethyl; D-2-(4-aminophenyl)-1,1-ethyl; D-2-(4-chlorophenyl)-1,1-ethyl; D-2-(4-ethoxyphenyl)-1,1-ethyl; D-2-(4-fluorophenyl)-1,1-ethyl; D-2-(4-hydroxyphenyl)-1,1-ethyl; D-2-(N-formyl-indol-3-yl)-1,1-ethyl; D-2-carboxamido-1,1-ethyl; D-2-carboxamido-1,2-ethyl; D-2-carboxy-1,2-ethyl; D-2-cyclohexyl-1,1-ethyl; D-2-hydroxy-1,1-ethyl; D-2-hydroxy-1,1-propyl; D-2-mercapto-1,1-ethyl; D-2-methyl-1,1-butyl; D-2-methyl-1,1-propyl; D-2-phenyl-1,1-ethyl; D-3-carboxamido-1,1-propyl; D-3-carboxamido-1,3-propyl; D-3-carboxy-1,1-propyl; D-3-carboxy-1,3-propyl; D-3-methyl-1,1-butyl; D-4-ureido-1,1-butyl; D-5-(9-fluorenylmethoxycarboxamido)-1,1-pentyl; D-5-acetamido-1,1-pentyl; D-5-amino-1,1-pentyl; D-methylthio-1,1-propyl; D-phenylmethyl; D-t-butylmethyl; L-1,1-butyl; L-1,1-ethyl; L-1,1-pentyl; L-1,1-propyl; L-1-amino-1,5-pentyl; L-2-(2-naphthyl)-1,1-ethyl; L-2-(2-thienyl)-1,1-ethyl; L-2-(3-pyridyl)-1,1-ethyl; L-2-(4-aminophenyl)-1,1-ethyl; L-2-(4-chlorophenyl)-1,1-ethyl; L-2-(4-ethoxyphenyl)-1,1-ethyl; L-2-(4-fluorophenyl)-1,1-ethyl; L-2-(4-hydroxyphenyl)-1,1-ethyl; L-2-(N-formyl-indol-3-yl)-1,1-ethyl; L-2-carboxamido-1,1-ethyl; L-2-carboxamido-1,2-ethyl; L-2-carboxy-1,1-ethyl; L-2-carboxy-1,2-ethyl; L-2-cyclohexyl-1,1-ethyl; L-2-hydroxy-1,1-ethyl; L-2-hydroxy-1,1-propyl; L-2-mercapto-1,1-ethyl; L-2-methyl-1,1-butyl; L-2-methyl-1,1-propyl; L-2-phenyl-1,1-ethyl; L-3-carboxamido-1,1-propyl; L-3-carboxamido-1,3-propyl; L-3-carboxy-1,1-propyl; L-3-carboxy-1,3-propyl; L-3-methyl-1,1-butyl; L-4-ureido-1,1-butyl; L-5-acetamido-1,1-pentyl; L-5-amino-1,1-pentyl; 5-(4-amino-(3,4-dihydro-3-alkoxy)-2quinolinoyl)-1,1-pentyl; L-methylthio-1,1-propyl; L-phenylmethyl; L-t-butylmethyl; and methylene;

$R^2$ is selected from the group consisting of hydroxy; methoxy; phenoxy; benzyloxy; acetoxy; and 4-chlorophenoxy;

$R^3$ $R^4$, $R^5$, $R^6$ are, selected from the group consisting of when each are, independently, a hydrogen atom; $R^3$ and $R^6$ are each hydrogen when $R^4$ and $R^5$ are together methylenedioxy or $R^4$ and $R^5$ are each, independently, methoxy; $R^3$, $R^4$ and $R^6$ are each, independently, a hydrogen atom when $R^5$ is chloro or methoxy; and $R^3$ is methoxy when $R^4$, $R^5$ and $R^6$ are each, independently, a hydrogen atom;

$R^7$ is selected from the group consisting of nalidixoyl; 2-phenyl-4-quinolinecarboxy; 2-pyrazinecarboxy; niflumoyl, 4-nitrophenylacetyl; 4-(4-nitrophenyl)butyroyl; (3,4-dimethoxyphenyl)acetyl; 3,4-(methylenedioxy)phenylacetyl; 4-nitrocinnamoyl; 3,4,-(methylenedioxy)cinnamoyl; 3,4,5-trimethoxycinnamoyl; benzoyl; 2-chlorobenzoyl; 2-nitrobenzoyl; 2-(p-toluoyl)benzoyl; 2,4-dinitrophenylacetyl; 3-(3,4,5-trimethoxyphenyl)-propionyl; 4-biphenylacetyl; 1-napthylacetyl; (2-napthoxy)acetyl; trans-cinnamoyl; picolinyl; 3-amino-4-hydroxybenzoyl; (4-pyridylthio)acetyl; 2,4-dichlorobenzoyl; 3,4-dichlorobenzoyl; 4-biphenylcarboxy; thiophenoxyacetyl; 1-benzoylpropionyl; phenylacetyl; hydrocinnamoyl; 3,3-diphenylpropionyl; 3,3,3-triphenylpropionyl; 4-phenylbutyryl; phenoxyacetyl; (±)-2-phenoxypropionyl; 2,4-dimethoxybenzoyl; 3,4-dimethoxybenzoyl; 3,4-dihydroxybenzoyl; 2,4-dihydroxybenzoyl; 3,4,5-trimethoxybenzoyl; 3,4,5-triethoxybenzoyl; 3,4,5-trihydroxybenzoyl; 2-benzoylbenzoyl; 1-napthoyl; xanthene-9-carboxy; 4-chloro-2-nitrobenzoyl; 2-chloro-4-nitrobenzoyl; 4-chloro-3-nitrobenzoyl; 2-chloro-5-nitrobenzoyl; 4-dimethylaminobenzoyl; 4-(diethylamino)benzoyl; 4-nitrobenzoyl; 3-(dimethylamino)benzoyl; p-methylbenzoyl; p-methoxybenzoyl; trimethylacetyl; tert-butylacetyl; (−)-menthoxyacetyl; cyclohexanecarboxy; cyclohexylacetyl; dicyclohexylacetyl; cyclohexanebutyroyl; cycloheptanecarboxy; 13-isopropylpodocarpa-7,13-dien-15-oyl; acetyl; octanoyl; (methylthio)acetyl; 3-nitropropionyl; 4-amino-3-hydroxybenzoyl; 3-(2-methyl-4-nitro-1-imidizoyl)propionyl; 2-furoyl; (s)(−)-2-pyrrolidone-5-carboxy; (2-pyrimidylthio)acetyl; 4-methoxy-2-quinolinecarboxy; 1-adamantanecarboxy; piperonoyl; 5-methyl-3-phenylisoxazole-4-carboxy; rhodanine-3-acetyl; 2-norbornaneacetyl; nicotinoyl; 9-oxo-9H-thioxanthene-3-carboxyl-10,10 dioxide; 2-thiophenecarboxy; 5-nitro-2-furanoyl; indole-3-acetyl; isonicotinoyl; 3α-hydroxy-5β-cholan-24-oyl; (3α,7α,12α)-trihydroxy-5β-cholan-24-oyl; (3α,5β-12α)-3,12, dihydroxy-5-cholan-24-oyl; (3α,5β,6α)-3,6-dihydroxy-cholan-24-oyl; L-alaninyl; L-cysteinyl; L-aspartinyl; L-glutaminyl; L-phenylalaninyl; glycinyl; L-histidinyl; L-isoleucinyl; L-lyscinyl; L-leucinyl; L-methionylsulfoxide; L-methionyl; L-asparginyl; L-prolinyl; L-glutaminyl; L-arganinyl; L-serinyl; L-threoninyl; L-valinyl; L-tryptophanoyl; L-tyrosinyl; D-alaninyl; D-cysteinyl; D-aspartinyl; D-glutaminyl; D-phenylalaninyl; glycinyl; D-histidinyl; D-isoleucinyl; D-lyscinyl; D-leucinyl; D-methionylsulfoxide; D-methionyl; D-asparginyl; D-prolinyl; D-glutaminyl; D-arganinyl; D-serinyl; D-threoninyl; D-valinyl; D-tryptophanoyl; D-tyrosinyl; 2-aminobutyroyl; 4-aminobutyroyl; 2-aminoisobutyroyl; L-norleucinyl; D-norleucinyl; 6-aminohexanoyl; 7-aminoheptanoyl; thioprolinyl; L-norvalinyl; D-norvalinyl; α-ornithinyl; methionyl sulfonyl; L-naphthylalaninyl; D-naphthylalaninyl; L-phenylglycinyl; D-phenylglycinyl; β-alaninyl; L-cyclohexylalaninyl; D-cyclohexylalaninyl; hydroxyprolinyl; nitrophenylalaninyl; dehydroprolinyl; 3-hydroxy-1-propanesulfonyl; 1-propanesulfonyl; 1-octanesulfonyl; perfluoro-1-octanesulfonly; (+)-10-camphorsulfonyl; (−)-10-camphorsulfonyl; benzenesulfonyl; 2-nitrobenzenesulfonyl; p-toluenesulfonyl; 4-nitrobenzenesulfonyl; n-acetylsulfanilyl; 2,5-dichlorobenzenesulfonyl; 2,4-dinitrobenzenesulfonyl; 2-mesitylenesulfonyl; and 2-napthalenesulfonyl;

$R^8$ is a hydrogen atom; and

Y is $C(O)NH_2$.

5. The library of claim 1, wherein:

$R^1$ is selected from the group consisting of 1,2-ethyl; 1,3-propyl; 1,4-butyl; 1,5-pentyl; 1,6-hexyl; 1-methyl-1,1-ethyl; 3-aminobenzoyl; 4-amino-2-chlorobenzoyl; 4-aminobenzoyl; 4-aminomethylbenzoyl; D-1,1-butyl; D-1,1-ethyl; D-1,1-pentyl; D-1,1-propyl; D-1-amino-1,5-pentyl; D-2-(2-naphthyl)-1,1-ethyl; D-2-(2-thienyl)-1,1-ethyl; D-2-(3-pyridyl)-1,1-ethyl; D-2-(4-aminophenyl)-1,1-ethyl; D-2-(4-chlorophenyl)-1,1-ethyl; D-2-(4-ethoxyphenyl)-1,1-ethyl; D-2-(4-fluorophenyl)-1,1-ethyl; D-2-(4-hydroxyphenyl)-1,1-ethyl; D-2-(N-formyl-indol-3-yl)-1,1-ethyl; D-2-carboxamido-1,1-ethyl; D-2-carboxamido-1,2-ethyl; D-2-carboxy-1,2-ethyl; D-2-cyclohexyl-1,1-ethyl; D-2-hydroxy-1,1-ethyl; D-2-hydroxy-1,1-propyl; D-2-mercapto-1,1-ethyl; D-2-methyl-1,1-butyl; D-2-methyl-1,1-propyl; D-2-phenyl-1,1-ethyl; D-3-carboxamido-1,1-propyl; D-3-carboxamido-1,3-propyl; D-3-carboxy-1,1-propyl; D-3-carboxy-1,3-propyl; D-3-methyl-1,1-butyl; D-4-ureido-1,1-butyl; D-5-(9-fluorenylmethoxycarboxamido)-1,1-pentyl; D-5-acetamido-1,1-pentyl; D-5-amino-1,1-pentyl; D-methylthio-1,1-propyl; D-phenylmethyl; D-t-butylmethyl; L-1,1-butyl; L-1,1-ethyl; L-1,1-pentyl; L-1,1-propyl; L-1-amino-1,5-pentyl; L-2-(2-naphthyl)-1,1-ethyl; L-2-(2-thienyl)-1,1-ethyl; L-2-(3-pyridyl)-1,1-ethyl; L-2-(4-aminophenyl)-1,1-ethyl; L-2-(4-chlorophenyl)-1,1-ethyl; L-2-(4-ethoxyphenyl)-1,1-ethyl; L-2-(4-fluorophenyl)-1,1-ethyl; L-2-(4-hydroxyphenyl)-1,1-ethyl; L-2-(N-formyl-indol-3-yl)-1,1-ethyl; L-2-carboxamido-1,1-ethyl; L-2-carboxamido-1,2-ethyl; L-2-carboxy-1,1-ethyl; L-2-carboxy-1,2-ethyl; L-2-cyclohexyl-1,1-ethyl; L-2-hydroxy-1,1-ethyl; L-2-hydroxy-1,1-propyl; L-2-mercapto-1,1-ethyl; L-2-methyl-1,1-butyl; L-2-methyl-1,1-propyl; L-2-phenyl-1,1-ethyl; L-3-carboxamido-1,1-propyl; L-3-carboxamido-1,3-propyl; L-3-carboxy-1,1-propyl; L-3-carboxy-1,3-propyl; L-3-methyl-1,1-butyl; L-4-ureido-1,1-butyl; L-5-acetamido-1,1-pentyl; L-5-amino-1,1-pentyl; 5-(4-amino-(3,4-dihydro-3-alkoxy)-2quinolinoyl)-1,1-pentyl; L-methylthio-1,1-propyl; L-phenylmethyl; L-t-butylmethyl; and methylene;

$R^2$ is selected from the group consisting of hydroxy; methoxy; phenoxy; benzyloxy; acetoxy; and 4-chlorophenoxy;

$R^3$ $R^4$, $R^5$, $R^6$ are, selected from the group consisting of when each are, independently, a hydrogen atom; $R^3$ and $R^6$ are each hydrogen when $R^4$ and $R^5$ are together methylenedioxy or $R^4$ and $R^5$ are each, independently, methoxy; $R^3$, $R^4$ and $R^6$ are each, independently, a hydrogen atom when $R^5$ is chloro or methoxy; and $R^3$ is methoxy when $R^4$, $R^5$ and $R^6$ are each, independently, a hydrogen atom;

$R^7$ and $R^8$ are, independently, selected from the group consisting of nalidixoyl; 2-phenyl-4-quinolinecarboxy; 2-pyrazinecarboxy; niflumoyl; 4-nitrophenylacetyl; 4-(4-nitrophenyl)butyroyl; (3,4-dimethoxyphenyl)-acetyl; 3,4-(methylenedioxy)phenylacetyl; 4-nitrocinnamoyl; 3,4,-(methylenedioxy)cinnamoyl; 3,4,5-trimethoxycinnamoyl; benzoyl; 2-chlorobenzoyl; 2-nitrobenzoyl; 2-(p-toluoyl)benzoyl; 2,4-dinitrophenylacetyl; 3-(3,4,5-trimethoxyphenyl)-propionyl; 4-biphenylacetyl; 1-napthylacetyl; (2-napthoxy)acetyl; trans-cinnamoyl; picolinyl; 3-amino-4-hydroxybenzoyl; (4-pyridylthio)acetyl; 2,4-dichlorobenzoyl; 3,4-dichlorobenzoyl; 4-biphenylcarboxy; thiophenoxyacetyl; 1-benzoylpropionyl; phenylacetyl; hydrocinnamoyl; 3,3-diphenylpropionyl; 3,3,3-triphenylpropionyl; 4-phenylbutyryl; phenoxyacetyl; (±)-2-phenoxypropionyl; 2,4-dimethoxybenzoyl; 3,4-dimethoxybenzoyl; 3,4-dihydroxybenzoyl; 2,4-dihydroxybenzoyl; 3,4,5-trimethoxybenzoyl; 3,4,5-triethoxybenzoyl; 3,4,5-trihydroxybenzoyl; 2-benzoylbenzoyl; 1-napthoyl; xanthene-9-carboxy; 4-chloro-2-nitrobenzoyl; 2-chloro-4-nitrobenzoyl; 4-chloro-3-nitrobenzoyl; 2-chloro-5-nitrobenzoyl; 4-dimethylaminobenzoyl; 4-(diethylamino)benzoyl; 4-nitrobenzoyl; 3-(dimethylamino)benzoyl; p-methylbenzoyl; p-methoxybenzoyl; trimethylacetyl; tert-butylacetyl; (−)-menthoxyacetyl; cyclohexanecarboxy; cyclohexylacetyl; dicyclohexylacetyl; cyclohexanebutyroyl; cycloheptanecarboxy; 13-isopropylpodocarpa-7,13-dien-15-oyl; acetyl; octanoyl; (methylthio)acetyl; 3-nitropropionyl; 4-amino-3 hydroxybenzoyl; 2-methyl-4-nitro-1-imidizole propionyl; 2-furoyl; (s)(−)-2-pyrrolidone-5-carboxy; (2-pyrimidylthio)acetyl; 4-methoxy-2-quinolinecarboxy; 1-adamantanecarboxy; piperonoyl; 5-methyl-3-phenylisoxazole-4-carboxy; rhodanine-3-acetyl; 2-norbornaneacetyl; nicotinoyl; 9-oxo-9H-thioxanthene-3-carboxyl-10,10 dioxide; 2-thiophenecarboxy; 5-nitro-2-furanoyl; indole-3-acetyl; isonicotinoyl; 3α-hydroxy-5β-cholan-24-oyl; (3α,7α,12α)-trihydroxy-5β-cholan-24-oyl; (3α,5β-12α)-3,12, dihydroxy-5-cholan-24-oyl; (3α,5β,6α)-3,6-dihydroxy-cholan-24-oyl; L-alaninyl; L-cysteinyl; L-aspartinyl; L-glutaminyl; L-phenylalaninyl; glycinyl; L-histidinyl; L-isoleucinyl; L-lyscinyl; L-leucinyl; L-methionylsulfoxide; L-methionyl; L-asparginyl; L-prolinyl; L-glutaminyl; L-arganinyl; L-serinyl; L-threoninyl; L-valinyl; L-tryptophanoyl; L-tyrosinyl; D-alaninyl; D-cysteinyl; D-aspartinyl; D-glutaminyl; D-phenylalaninyl; glycinyl; D-histidinyl; D-isoleucinyl; D-lyscinyl; D-leucinyl; D-methionylsulfoxide; D-methionyl; D-asparginyl; D-prolinyl; D-glutaminyl; D-arganinyl; D-serinyl; D-threoninyl; D-valinyl; D-tryptophanoyl; D-tyrosinyl; 2-aminobutyroyl; 4-aminobutyroyl; 2-aminoisobutyroyl; L-norleucinyl; D-norleucinyl; 6-aminohexanoyl; 7-aminoheptanoyl; thioprolinyl; L-norvalinyl; D-norvalinyl; α-ornithinyl; methionyl sulfonyl; L-naphthylalaninyl; D-naphthylalaninyl; L-phenylglycinyl; D-phenylglycinyl; β-alaninyl; L-cyclohexylalaninyl; D-cyclohexylalaninyl; hydroxyprolinyl; nitrophenylalaninyl; dehydroprolinyl; 3-hydroxy-1-propanesulfonyl; 1-propanesulfonyl; 1-octanesulfonyl; perfluoro-1-octanesulfonly; (+)-10-camphorsulfonyl; (−)-10-camphorsulfonyl; benzenesulfonyl; 2-nitrobenzenesulfonyl; p-toluenesulfonyl; 4-nitrobenzenesulfonyl; n-acetylsulfanilyl; 2,5-dichlorobenzenesulfonyl; 2,4-dinitrobenzenesulfonyl; 2-mesitylenesulfonyl; and 2-napthalenesulfonyl; and Y is $C(O)NH_2$.

6. A library of two or more tetrahydro-quinoline compounds of the formula:

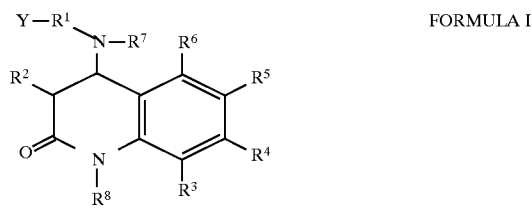

FORMULA I wherein:

$R^1$ is selected from the group consisting of $C_1$ to $C_6$ alkyl, $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_7$ to $C_{12}$ phenylalkyl, $C_7$ to $C_{12}$ substituted phenylalkyl or a group of the formula:

$$-(CH)_n-Ar-(CH_2)_m-$$

wherein n and m are independently selected from a number 0 to 6; and Ar is an aryl group selected from the group consisting of phenyl, substituted phenyl, heteroaryl and substituted heteroaryl;

$R^2$ is selected from the group consisting of hydroxy, $C_1$ to $C_7$ alkoxy, $C_1$ to $C_7$ substituted alkoxy, $C_1$ to $C_7$ acyloxy, $C_7$ to $C_{12}$ phenylalkoxy, $C_7$ to $C_2$ substituted phenylalkoxy, phenoxy, substituted phenoxy, phthalimide, substituted phthalimide, amino, protected amino, (monosubstituted)amino, (disubstituted)amino, $C_1$ to $C_4$ alkylthio, $C_1$ to $C_4$ substituted alkylthio, $C_1$ to $C_4$ alkylsulfonyl, $C_1$ to $C_4$ substituted alkylsulfonyl, $C_1$ to C, alkylsulfoxide, $C_1$ to $C_4$ substituted alkylsulfoxide, phenylthio, substituted phenylthio, phenylsulfoxide, substituted phenylsulfoxide, phenylsulfonyl and substituted phenylsulfonyl;

$R^3$, $R^4$, $R^5$ and $R^6$ are, independently, selected from the group consisting of amino, protected amino, (monosubstituted)amino, protected (monosubstituted) amino, and (disubstituted)amino;

$R^7$ and $R^8$ are, independently, selected from the group consisting of a hydrogen atom, $C_1$ to $C_6$ alkyl, $C_1$ to $C_6$ substituted alkyl, $C_1$ to $C_7$ acyl, $C_1$ to $C_7$ substituted acyl, phenylsulfonyl, substituted phenylsulfonyl, $C_1$ to $C_4$ alkylsulfonyl, $C_1$ to $C_4$ substituted alkylsulfonyl, $C_1$ to $C_6$ alkylaminocarbonyl, $C_1$ to $C_6$ substituted alkylaminocarbonyl, phenylaminocarbonyl, and substituted phenylaminocarbonyl; and Y is selected from the group consisting of $CO_2H$, OH, SH, $NHR^9$, $C(O)NHR^9$, $CH_2OH$, $CH_2NH_2$, $CH_2NHR^9$ and a functionalized resin, wherein $R^9$ is a hydrogen atom, $C_1$ to $C_6$ alkyl and $C_1$ to $C_6$ substituted alkyl; or a salt of the tetrahydro-quinoline compounds.

* * * * *

UNITED STATES PATENT AND TRADEMARK OFFICE
CERTIFICATE OF CORRECTION

PATENT NO. : 5,840,500  Page 1 of 3
DATED : Nov. 24, 1998
INVENTOR(S) : Pei et al.

It is certified that error appears in the above-identified patent and that said Letters Patent is hereby corrected as shown below:

In column 3, line 25, please delete "C1" and replace therefor with --$C_1$--.

In column 3, line 41, please delete "C1" and replace therefor with --$C_1$--.

In column 4, line 29, please delete "$Cl_2$" and replace therefor with --$C_{12}$--.

In column 8, line 13, please delete ")acety l," and replace therefor with --)acetyl,--..

In column 24, line 67, please delete "menthoxyacetic" and replace therefor with --methoxyacetic--.

In column 25, line 10, please delete "nicotinnic" and replace therefor with --nicotinic--.

In column 25, line 28, please delete "a-ornithine," and replace therefor with --α-ornithine,--.

UNITED STATES PATENT AND TRADEMARK OFFICE
CERTIFICATE OF CORRECTION

PATENT NO. : 5,840,500  
DATED : Nov. 24, 1998  
INVENTOR(S) : Pei et al.

Page 2 of 3

It is certified that error appears in the above-identified patent and that said Letters Patent is hereby corrected as shown below:

In column 25, line 34, please delete "octanesulfonly" and replace therefor with --octanesulfonyl--.

In column 25, line 35, please delete "benzenesulfonly" and replace therefor with --benzenesulfonyl--.

In column 25, line 37, please delete "n-acetylsulfanilyl" and replace therefor with --n-acetylsulfonyl--.

In column 30, line 14, please delete "Acids" and replace therefor with --Acid--.

In column 31, line 22, please delete "6 1.23(d, 3H)," and replace therefor with --δ 1.23(d, 3H),--.

In column 33, line 8, please delete "4,58(m," and replace therefor with --4.58(m,--.

In column 41, line 27, please insert a space between "40." and "As".

UNITED STATES PATENT AND TRADEMARK OFFICE
CERTIFICATE OF CORRECTION

PATENT NO.  : 5,840,500
DATED       : Nov. 24, 1998
INVENTOR(S) : Pei et al.

It is certified that error appears in the above-identified patent and that said Letters Patent is hereby corrected as shown below:

In column 42, claim 1, line 29, please delete "$R^1$" and replace therefor with --$R^2$--.

In column 43, claim 2, line 10, please delete "claim 6" and replace therefor with --claim 1--.

In column 43, claim 2, line 24, please delete "alkoxy $C_1$" and replace therefor with --alkoxy, $C_1$--.

Signed and Sealed this

Sixth Day of July, 1999

Attest:

Q. TODD DICKINSON

Attesting Officer

Acting Commissioner of Patents and Trademarks